United States Patent
Chen et al.

(10) Patent No.: US 12,144,822 B2
(45) Date of Patent: Nov. 19, 2024

(54) MIR-17~92 AS THERAPEUTIC OR DIAGNOSTIC TARGET OF MOTOR NEURON (MN) DEGENERATION DISEASES

(71) Applicant: Academia Sinica, Taipei (TW)

(72) Inventors: Jun-An Chen, Taipei (TW); Kuan-Chih Peng, Taipei (TW); Ying-Tsen Tung, Taipei (TW)

(73) Assignee: ACADEMIA SINICA, Taipei (TW)

( * ) Notice: Subject to any disclaimer, the term of this patent is extended or adjusted under 35 U.S.C. 154(b) by 963 days.

(21) Appl. No.: 17/043,891

(22) PCT Filed: Apr. 2, 2019

(86) PCT No.: PCT/US2019/025406
§ 371 (c)(1),
(2) Date: Sep. 30, 2020

(87) PCT Pub. No.: WO2019/195304
PCT Pub. Date: Oct. 10, 2019

(65) Prior Publication Data
US 2021/0145859 A1 May 20, 2021

Related U.S. Application Data

(60) Provisional application No. 62/652,127, filed on Apr. 3, 2018.

(51) Int. Cl.
| | |
|---|---|
| *C07H 21/02* | (2006.01) |
| *A61K 31/7105* | (2006.01) |
| *A61K 47/46* | (2006.01) |
| *A61P 21/00* | (2006.01) |
| *A61P 25/00* | (2006.01) |
| *C12N 15/113* | (2010.01) |

(52) U.S. Cl.
CPC .......... *A61K 31/7105* (2013.01); *A61K 47/46* (2013.01); *A61P 21/00* (2018.01); *A61P 25/00* (2018.01); *C12N 15/113* (2013.01); *C12N 2310/141* (2013.01)

(58) Field of Classification Search
CPC .......................... C12N 15/113; C12N 2310/141
See application file for complete search history.

(56) References Cited

U.S. PATENT DOCUMENTS

| | | | |
|---|---|---|---|
| 8,202,848 | B2 | 6/2012 | Williams et al. |
| 9,359,607 | B2 | 6/2016 | Hornstein et al. |
| 2010/0130574 | A1 | 5/2010 | Eggan et al. |
| 2015/0197810 | A1 | 7/2015 | Hornstein et al. |

FOREIGN PATENT DOCUMENTS

| | | |
|---|---|---|
| CN | 101988091 A | 3/2011 |
| CN | 104800860 A | 7/2015 |
| JP | 2015133919 A | 7/2015 |
| WO | 2010064248 A2 | 6/2010 |
| WO | 2015143078 A1 | 9/2015 |
| WO | 2016196978 A1 | 12/2016 |

OTHER PUBLICATIONS

Tung et al. (Cell Reports, 2015, 11, 1305-1318).*
Herrera-Carrillo et al. (Human Gene Therapy Methods, 2017, 28, 4, 177-190).*
Rudnick et al. (PNAS, 114(39), 2017, E8294-E8303).*
Chen JA & Wichterle H (2012) Apoptosis of limb innervating motor neurons and erosion of motor pool identity upon lineage specific dicer inactivation. Frontiers in neuroscience 6:69.
Eitan C & Hornstein E (2016) Vulnerability of microRNA biogenesis in FTD-ALS. Brain Res 1647:105-111.
Hou, L. et al., (2015) Screening of SOD1, FUS and TARDBP genes in patients with amyotrophic lateral sclerosis in central-southern china, Scientific reports, 2016, vol. 6, article 32478, pp. 1-7.
Kikuchi H, et al. (2006) Spinal cord endoplasmic reticulum stress associated with a microsomal accumulation of mutant superoxide dismutase-1 in an ALS model. Proceedings of the National Academy of Sciences of the United States of America 103(15):6025-6030.
Toli, D. et al., (2015) Modeling amytrophic lateral sclersis in pure human iPSc-derived motor neurons isolated by a novel FACs double selection technique, Neurobiology of Disease, 2015, No. 82, pp. 269-280.
Tung YT, et al. (2015) Mir-17~92 Governs Motor Neuron Subtype Survival by Mediating Nuclear PTEN. Cell reports 11(8):1305-1318.
Williams AH, et al. (2009) MicroRNA-206 delays ALS progression and promotes regeneration of neuromuscular synapses in mice. Science 326(5959):1549-1554.
Zou Z Y et al. (2013) Screening for C9orf72 repeat expansion Neurobiology of aging, 2013, vol. 34, No. 6, pp. 1710. e5-1710.e6.
Extended European Search Report issued in EP Patent Application No. 19780579.9 dated Nov. 5, 2021.
Hou, Lihua et al.: "Screening of SOD1, FUS and TARDBP genes in patients with amyotrophic lateral sclerosis in central-southern China", Scientific Reports, vol. 6, No. 1, Sep. 8, 2016 (Sep. 8, 2016), pp. 1-7, XP055640974.
Ichiyanagi, Naoki et al.: "Establishment of In Vitro FUS-Associated Familial Amyotrophic Lateral Sclerosis Model Using Human Induced Pluripotent Stem Cells", Stem Cell Reports, vol. 6, No. 4, Apr. 1, 2016 (Apr. 1, 2016), pp. 496-510, XP055403116.

(Continued)

*Primary Examiner* — Amy Rose Hudson
(74) *Attorney, Agent, or Firm* — Prosyla Group PC

(57) ABSTRACT

The present disclosure relates to mir-17~92 as a candidate therapeutic or diagnostic target of motor neuron (MN) degeneration diseases. Expression of mir-17~92 is sustained throughout adulthood in spinal MNs and specifically decreases before the onset of MN loss in $SOD1_{G93A}$ mice. Accordingly, mir-17~92 can be used as a candidate therapeutic target for ALS.

8 Claims, 30 Drawing Sheets

(56) References Cited

OTHER PUBLICATIONS

Magri, Francesca et al: "miRNA in spinal muscular atrophy pathogenesis and therapy", Journal of Cellular and Molecular Medicine, Nov. 21, 2017 (Nov. 21, 2017), XP055532283.
Sathiya, Sekar et al.: "Elevated nuclear phosphatase and tensin homolog (PTEN) and altered insulin signaling in substantia nigral region of patients with Parkinson's disease", Neuroscience Letters, Elsevier, Amsterdam, NL, vol. 666, Dec. 26, 2017 (Dec. 26, 2017), pp. 139-143, XP085344583.
Tung, Ying-Tsen et al.: "Mir-17 92 Governs Motor Neuron Subtype Survival by Mediating Nuclear PTEN", Cell Reports, vol. 11, No. 8. May 26, 2015 (May 26, 2015), pp. 1305-1318, XP055640958.
Tung, Ying-Tsen et al: "Mir-17~92 Confers Motor Neuron Subtype Differential Resistance to ALS-Associated Degeneration", Cell Stem Cell, Elsevier, Cell Press, Amsterdam, NL, vol. 25, No. 2, May 30, 2019 (May 30, 2019), p. 193, XP085754262.
Zou, Zhang-Yu et al: "Screening for C9orf72 repeat expansions in Chinese amyotrophic lateral sclerosis patients", Neurobiology of Aging, vol. 34, No. 6, Dec. 20, 2011 (Dec. 20, 2012), pp. 1710.e5-1710.e6, XP055640964.
Office Action dated Apr. 15, 2023, from Chinese Patent Application No. 201980024546.1. English translation provided.

\* cited by examiner

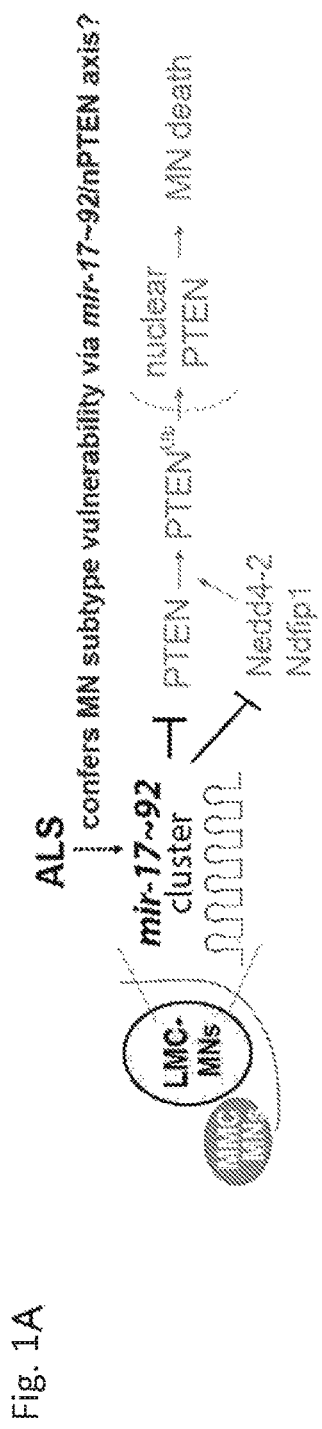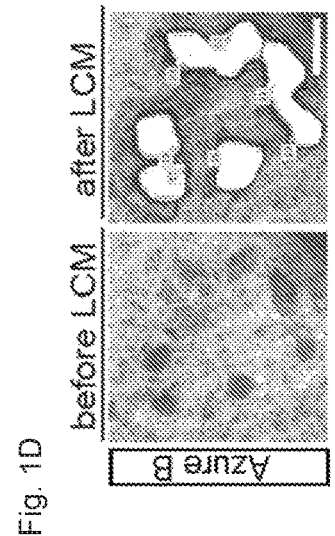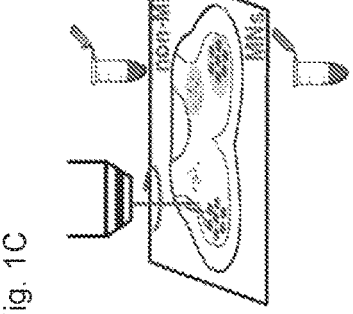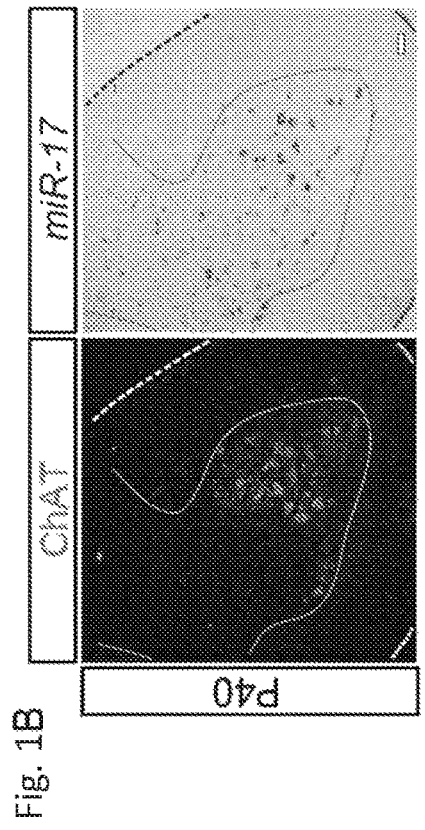
Fig. 1A
Fig. 1B
Fig. 1C
Fig. 1D

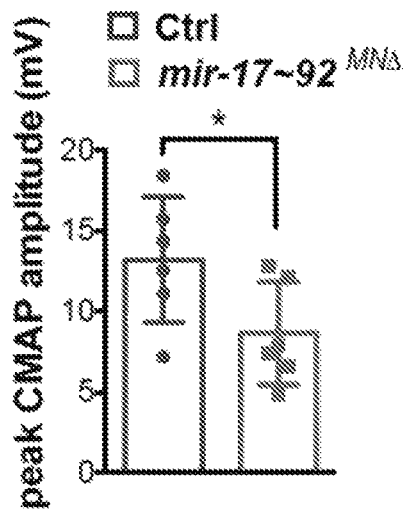

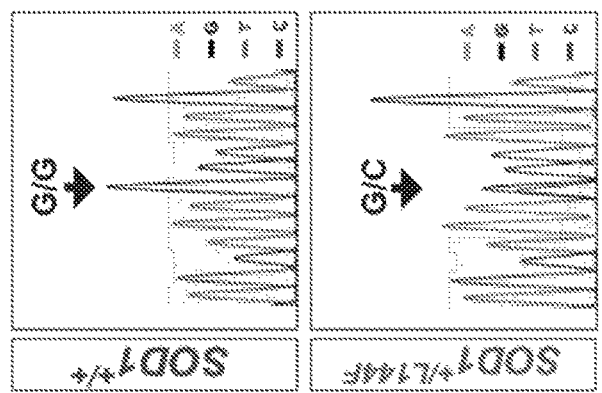
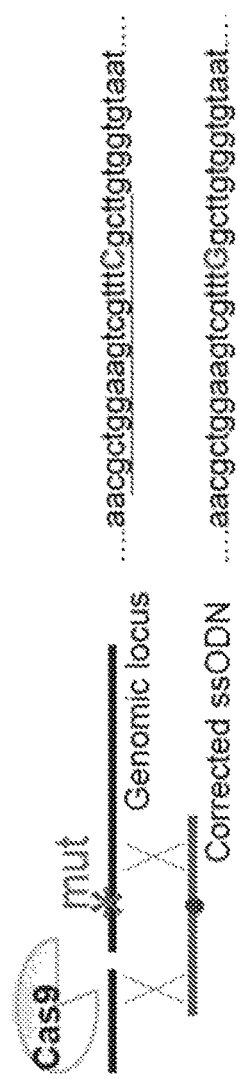
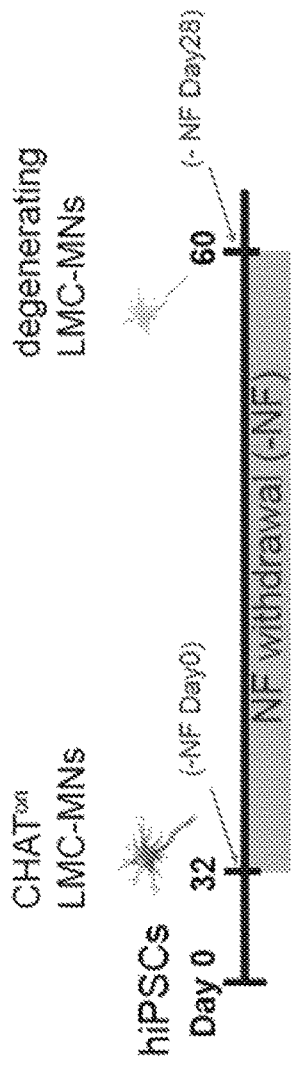
Fig. 5A
Fig. 5B
Fig. 5C

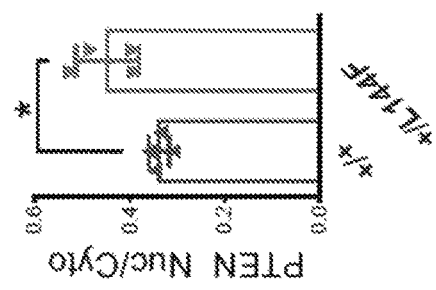
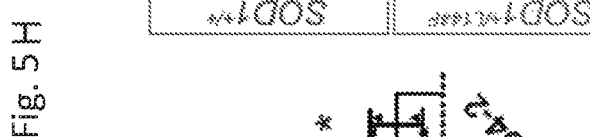
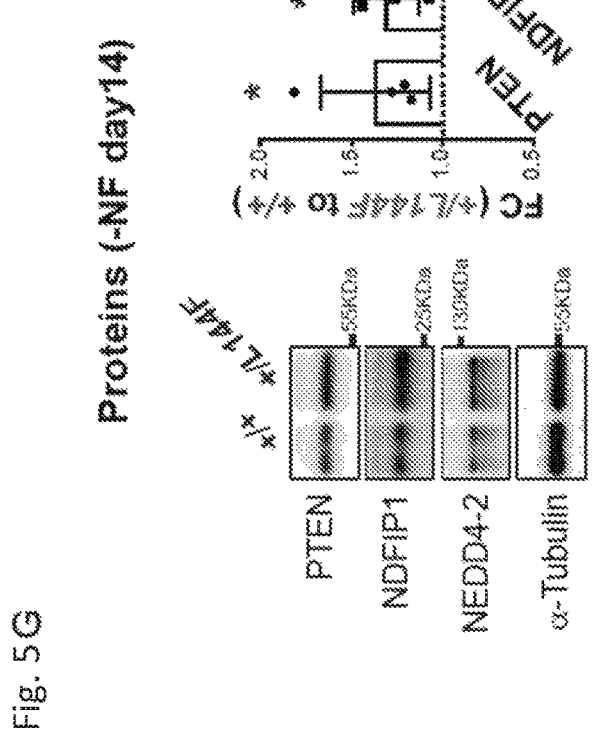
Fig. 5G
Fig. 5H

Fig. 7A  Ctrl: Olig2$^{Cre/+}$; ROSA26-LSL-mir17~92$^{fl/+ or fl/+}$
ALS: SOD1$^{G93A}$; ROSA26-LSL-mir17~92$^{fl/+ or fl/+}$ or SOD1$^{G93A}$; Olig2$^{Cre/+}$
ALS/mir-17~92$^{MN-OE}$: SOD1$^{G93A}$; Olig2$^{Cre/+}$; ROSA26-LSL-mir17~92$^{fl/+ or fl/+}$

MIR-17~92 AS THERAPEUTIC OR DIAGNOSTIC TARGET OF MOTOR NEURON (MN) DEGENERATION DISEASES

This application claims the benefit and priority to International Patent Application No. PCT/US19/25406, filed on Apr. 2, 2019, entitled "MIR-17~92 AS THERAPEUTIC OR DIAGNOSTIC TARGET OF MOTOR NEURON (MN) DEGENERATION DISEASES," which claims benefit to U.S. Provisional Application No. 62/652,127, filed on Apr. 3, 2018, entitled, "MIR-17~92 AS THERAPEUTIC OR DIAGNOSTIC TARGET OF MOTOR NEURON (MN) DEGENERATION DISEASES," the contents of which are incorporated by reference herewith in its entirety.

FIELD OF THE INVENTION

The present disclosure relates to the field of microRNA (miRNA), in particular mir-17~92 as a candidate therapeutic or diagnostic target of motor neuron (MN) degeneration diseases.

BACKGROUND OF THE INVENTION

ALS, also known as Lou Gehrig's disease, is a devastating adult-onset neurodegenerative disease that attacks upper and lower motor neurons. A progressive and ultimately fatal muscle paralysis ensues, usually causing death within 2 to 5 years of disease onset. ALS is mostly sporadic, but approximately 10% of cases are familial. The incidence rate is approximately 2-3 cases per 100,000 people per year worldwide. In about 75% of ALS patients, the distal limb-innervating MNs, especially the fast-twitch fatigable (FF) MNs that control rapid limb movements, are usually the first subtype of MNs to undergo degeneration, so patients initially experience weakness or atrophy in the arms or legs. Other MN subtypes are subsequently affected and, within 3 to 5 years, patients suffer complete paralysis and ultimately die due to respiratory failure. The only marketed drug (Riluzole) for treating ALS has modest effects, improving muscle function but having strong side-effects and no significant impact on patient survival. Recently, a new drug (Edaravone) was approved by the US Food & Drug Administration (FDA), but its efficacy remains to be evaluated. Thus far, there is no effective cure for this fatal disease.

Pathogenic mutations in several genes have been linked to familial and sporadic ALS, including SOD1, TARDBP, FUS/TLS, VAPB, OPTN and others. Dominant mutations in the superoxide dismutase 1 (SOD1) gene account for 15-20% of familial ALS (fALS). Although the exact pathological role of SOD1 in ALS remains unclear, a series of transgenic mice carrying fALS SOD1 mutants have been established, which recapitulate the pathological phenotype of ALS progression, including limb weakness as the first sign of disease onset, and provide a valuable model for studying ALS mechanisms. Cumulative studies in these fALS-SOD1 transgenic models suggest that dysregulation of multiple cellular mechanisms cooperatively contribute to ALS progression. One of the most intensively studied pathways is endoplasmic reticulum (ER) stress (Kikuchi H, et al. (2006) Spinal cord endoplasmic reticulum stress associated with a microsomal accumulation of mutant superoxide dismutase-1 in an ALS model. *Proceedings of the National Academy of Sciences of the United States of America* 103 (15):6025-6030), which is more prominently observed in vulnerable FF-MNs. RNA metabolism has also been linked to ALS pathology, as many of the identified disease-associated genes encode for RNA-binding proteins, such as TAR-DBP, FUS, and HNRNPA1. Interestingly, these disease-causing genes also participate in miRNA biogenesis and metabolism. Recent studies have further revealed that dysregulation of miRNA expression is manifested in ALS mouse models and patients (Eitan C & Hornstein E (2016) Vulnerability of microRNA biogenesis in FTD-ALS. *Brain Res* 1647:105-111).

MicroRNAs (miRNAs) are endogenous noncoding small RNAs that play critical roles in cell fate specification and neuronal survival in the spinal cord. A recent study revealed that pathogenic ALS-causing mutations are sufficient to inhibit Dicer complex activation, which is mediated by cytosolic macromolecular assembly of stress granules (SGs), leading to global down-regulation of miRNA biogenesis. Nevertheless, the precise functions and sets of miRNAs involved in ALS have not been fully established. Although loss of the muscle-specific miRNA, mir-206, can accelerate the onset of MN loss in a fALS-SOD1$_{G93A}$ mouse model (Williams A H, et al. (2009) MicroRNA-206 delays ALS progression and promotes regeneration of neuromuscular synapses in mice. *Science* 326(5959):1549-1554), it is still unclear if MN-specific miRNAs also participate in cell-autonomously regulating MN survival. Conditional loss of Dicer activity to block miRNA biogenesis in MN lineages of mouse embryos leads to selective degeneration of a subset of MNs, including limb-innervating MNs (Chen J A & Wichterle H (2012) Apoptosis of limb innervating motor neurons and erosion of motor pool identity upon lineage specific dicer inactivation. *Frontiers in neuroscience* 6:69). mir-17~92 is an MN-enriched miRNA cluster that is essential for controlling embryonic limb-innervating MN (LMC-MN) survival (Tung Y T, et al. (2015) Mir-17~92 Governs Motor Neuron Subtype Survival by Mediating Nuclear PTEN. *Cell reports* 11(8):1305-1318). This protective effect is mediated by inhibition of PTEN monoubiquitination by Nedd4-2 and Ndfip1, subsequent nuclear PTEN monoubiquitination by Nedd4-2 and Ndfip1, and subsequent nuclear PTEN translocalization.

SUMMARY OF THE INVENTION

The present disclosure surprisingly found that expression of mir-17~92 is sustained throughout adulthood in spinal MNs and that it specifically decreases before the onset of MN loss in SOD1$^{G93A}$ mice. This timing is concomitant with accumulation of nuclear PTEN in the spinal MNs of SOD1$^{G93A}$ mice. Importantly, overexpression of mir-17~92 in SOD1$^{G93A}$ MNs by either genetic approaches or adult scAAV9 delivery can significantly delay motor deficits and prolong lifespan. These findings define mir-17~92 as a candidate therapeutic target for ALS.

The present disclosure provides a method of treating or preventing a motor neuron degeneration disease in a subject, comprising administering to the subject a therapeutically or prophylactically effective amount of one or more genes or transgenes containing members of microRNA mir-17~92 cluster.

The present disclosure also provides a method of ameliorating motor deficits and prolonging lifespan of a subject with motor neuron degeneration disease, comprising administering to the subject an effective amount of one or more genes or transgenes containing members of microRNA mir-17~92. In one embodiment, the method can delay or prevent the onset of MN degeneration or reduce the risk of developing MN degeneration.

Certain embodiments include delivering one or more members of mir-17~92 cluster into central nervous system of the subject. Particularly, the one or more members of mir-17~92 cluster are delivered into spinal cord of the subject.

The present disclosure also provides a method of screening a drug protecting motor neuron subtypes in ALS in vitro, comprising (i) providing a stem cell line harboring a transgene comprising a fALS gene and a reporter gene, (ii) culturing a drug with the cell line; (iii) directing differentiation of the cell to the motor neuron cells and expression; and (iv) determining the said drug is effective to protect motor neuron subtypes in ALS if a motor neuron subtype is generated from the stem cell line.

The present disclosure further provides a method for diagnosis of motor neuron subtypes in ALS in a subject, comprising providing a biological sample and detecting the presence of one or more members of mir-17~92 cluster or nuclear PTEN, wherein the presence of dysregulated mir-17~92 members or nuclear PTEN is indicative of a diagnosis of motor neuron subtypes in ALS or a susceptibility to motor neuron subtypes in ALS in the subject.

The present disclosure further provides a kit for diagnosing motor neuron subtypes in ALS or susceptibility to motor neuron subtypes in ALS in a subject, comprising one or more reagents for detecting the presence of one or more members of mir-17~92 cluster or nuclear PTEN in a biological sample.

BRIEF DESCRIPTION OF THE DRAWINGS

FIGS. 1A to 1K show that mir-17~92 is required to maintain adult spinal MNs. (FIG. 1A) Illustration of how mir-17~92 controls PTEN subcellular localization by directly targeting the Nedd4-2 E3 ubiquitin ligase and its adaptor, Ndfip1, thus inhibiting pro-apoptotic nuclear PTEN (nPTEN) accumulation in developing LMC-MNs (Tung et al., 2015). This study further aims to reveal the potential involvement of the mir-17~92/nPTEN axis in MN degeneration in ALS. (FIG. 1B) Representative in situ hybridization of miR-17 expression in ChAT$^{on}$ MNs of lumbar spinal cords at P40. Dashed lines demarcate spinal cord margin and grey matter. Scale bar, 50 µm. (FIG. 1C) Schematic illustration of neuron distribution in adult spinal cord. Individual neuron cell bodies in the dorsal non-MN region and ventral-lateral MN region were laser capture microdissected and subjected to RNA extraction. (FIG. 1D) Representative frozen sections of the hemi-ventral horn region, stained with Azure B dye. Numbers in the right panel are automatically assigned by the microdissection software during microdissection. Scale bar, 50 µm. LCM, laser capture microdissection. (FIGS. 1E and 1F) qPCR analysis of ChAT and individual members of the mir-17~92 cluster in laser-microdissected cells. Dorsal non-MNs were captured as a control. (mean±s.d., n=4 mice. Two-tailed t-tests were performed between groups of interest. *P<0.05). FC: fold change. (FIGS. 1G and 1I) Immunostaining and quantification of ChAT$^{on}$ MN numbers in lumbar hemi-ventral horn sections of mir-17~92$^{MN\Delta}$ mice at P30 reveal a significant loss of MNs. (mean±s.d., n≥3 mice, *P<0.05, two-tailed t-tests). (FIGS. 1H and 1J) NMJs of gastrocnemius (GA) muscle at P30. mir-17~92$^{mN\Delta}$ mice manifest a significant reduction of NMJ innervations. α-BTX: α-bungarotoxin to detect nicotinic acetylcholine receptors (AChR). (mean±s.d., n=3 mice, *P<0.05, two-tailed t-tests). (K) Reduced neuromuscular function in mir-17~92$^{MN\Delta}$ mice, as revealed by evoked CMAPs in the GA muscle after stimulation of the sciatic nerve. Quantification of CMAPs was determined by calculating the maximum peak-to-peak values (mean±s.d, n=6 mice, *P<0.05, two-tailed t-tests).

(FIGS. 2A and 2B) Immunostaining and quantification of ChAT$^{on}$ MN numbers in sections of the lumbar hemi-ventral horn region reveal a significant loss of SOD1$^{G93A}$ MNs starting from P100. White dashed lines demarcate the spinal cord margin. Scale bar, 50 µm. (n≥4 mice, mean±s.d., *P<0.05, two-way ANOVA). (FIGS. 2C and 2D) Representative in situ hybridization of miR-17 expression in hemi-ventral lateral ChAT$^{on}$ MNs of lumbar spinal cords at different stages in (FIG. 2C) and quantification of miR-17 in (FIG. 2D). Note that miR-17 expression in SOD1$^{G93A}$ MNs started to decline at P80, before an obvious decrease in MNs in SOD1$^{G93A}$. Scale bar, 50 µm. (n≥4 mice, mean±s.d., *P<0.05, two-way ANOVA). (FIG. 2E) Schematic illustration of laser captures of frozen sections of ventral-lateral horn regions from control and SOD1$^{G93A}$ mice (see STAR METHODS). Only large MNs with a regular shape (intact MNs) were microdissected. (F~H) qPCR analyses of laser-captured MNs from SOD1$^{G93A}$ mice at P100. (FIG. 2F) The comparable expression of ChAT confirms that only intact MNs were collected. (FIG. 2G) SOD1$^{G93A}$ MNs exhibit down-regulation of mir-17~92 cluster members before MN loss. (FIG. 2H) Targets of mir-17~92, including PTEN, Ndfip1 and Nedd4-2, are up-regulated in SOD1$^{G93A}$ MNs. Data is shown as fold change (FC) of SOD1$^{G93A}$ MNs relative to Ctrl MNs. (mean±s.d., n=4 mice, *P<0.05, two-tailed t-tests). (FIG. 2I and FIG. 2J) Immunostaining of PTEN in ChAT$^{on}$ MNs of the lumbar spinal cord at different stages in (FIG. 2I). High magnifications of the highlighted PTEN cells in the yellow square are shown in the right-most panels. White dashed lines depict MN nuclei. Scale bar is 10 µm. (FIG. 2J) Quantification of nucleus-to-cytosol ratios of PTEN intensities in ChAT$^{on}$ MNs indicates an accumulation of nuclear PTEN in SOD1$^{G93A}$ MNs at P100. (mean±s.d., n≥4 mice, *P<0.05, two-way ANOVA).

(FIG. 3A) Schematic illustration of Ctrl and SOD1$^{G93A}$ ESC differentiation into postmitotic MNs with Hb9::RFP; Foxp1::GFP double reporters. To accelerate MN degeneration, cyclopiazonic acid (CPA) was introduced into MNs and the survival rate of MN subtypes was determined by flow cytometry. MNs treated with the vehicle (DMSO) were assessed as non-stressed controls. (FIGS. 3B and 3C) Survival rates of each MN subtype from Ctrl (blue) and SOD1$^{G93A}$ (red) Hb9::RFP; Foxp1::GFP ESCs were quantified by flow cytometry every 6 hrs after CPA or vehicle treatment. Percentages of each MN subpopulation at indicated time-points are normalized to that at 0 hr (i.e. right before treatment). SOD1$^{G93A}$ LMC-MNs undergo dramatic cell loss from 30 hr to 48 hr post-CPA treatment compared to treated Ctrl LMC-MNs. In contrast, both Ctrl and SOD1$^{G93A}$ non-LMC-MNs are more resistant to CPA treatment. (mean±s.d. from n=3 independent experiments. (FIGS. 3D-3G). FACS-purified MN subtypes at 24 hr post-treatment. Expression of mir-17~92 members (FIGS. 3D and 3E) and their targets (PTEN, Nedd4-2, Ndfip1) (FIGS. 3F and 3G) in each population was determined by qPCR. miRNA/mRNA levels were normalized to the corresponding Ctrl subtype. Dark purple highlights CPA-treated groups, whereas light purple denotes groups treated with vehicle alone. (mean±s.d. of at least 3 independent experiments, *P<0.05, two tailed t-tests).

(FIG. 4A) Immunostaining of PTEN subcellular localization in dissociated MNs after 24 hrs of CPA treatment. Red dashed lines depict the borders of MN nuclei. Scale bar, 10 μm. (FIG. 4B) Quantification of nucleus-to-cytosol ratios of PTEN average intensities in GFP$^{off}$RFP$^{on}$ non-LMC-MNs and GFP$^{on}$ RFP$^{on}$ LMC-MNs. (mean±s.d., n=3 independent experiments, *P<0.05, two tailed t-tests). (FIG. 4C) Schematic illustration of the stages performed during in ovo electroporation in the embryonic spinal cord. (FIG. 4D) Immunostaining of lumbar spinal cord sections demonstrates a reduction in Foxp1$^{on}$ LMC MNs at the electroporated side of GFP-PTEN-NLS$^{elec}$ spinal cords, whereas Lhx3$^{on}$ non-LMC neurons are more resistant to ectopic GFP-PTEN expression. (FIG. 4E) Quantification of Foxpri LMC MNs and Lhx3$^{on}$ non-LMC neurons. Data is shown as fold change of cell numbers in the electroporated side relative to the contralateral side. (mean±s.d., n=5/6 embryos, *P<0.05, one-way ANOVA).

FIGS. 5A to 5H show conserved dysregulation of the hsa-mir-17~92/nPTEN pathway in SOD1$^{+/L144F}$ human iPSC-derived MNs. (FIG. 5A) Schematic depiction of CRISPR-Cas9-mediated gene correction. The SOD1$^{+/L144F}$ mutation (G-to-C mutation) is highlighted in red. The guide RNA recognition sequence is underlined. A 99 nucleotide single-stranded oligonucleotide containing the corrected G (highlighted in blue) was introduced as a template for homology-directed repair (HDR). (FIG. 5B) The corrected base (G/C→G/G) in the Ctr1-SOD1$^{+/+}$ line was confirmed by DNA sequencing. (FIG. 5C) Timeline reflecting the schedule for neurotrophic factor (NF) withdrawal. (FIGS. 5D and 5E) ALS-SOD1$^{+/L144F}$ LMC-MNs are more vulnerable to NF withdrawal compared to Ctr1-SOD1$^{+/+}$ LMC-MNs during long-term culture. (FIG. 5D) Immunostaining to reveal LMC-MN (SMI32$^{on}$, ISL1$^{on}$ and FOXP1$^{on}$) at indicated time points during NF withdrawal. (FIG. 5E) The survival rates of LMC-MNs were determined by quantification of FOXP1$^{on}$ ISL1$^{on}$ numbers at indicated time-points after NF withdrawal and were normalized to that before NF withdrawal (–NF day 0). (mean±s.d., n=4 independent experiments, *P<0.05, two-way ANOVA). Scale bar, 100 μm. (FIG. 5F) Expression of hsa-mir-17~92 in long-term MN cultures at day 14 after NF withdrawal, as determined by qPCR. Data is shown as fold change (FC) of ALS-SOD1$^{+/L144F}$ relative to Ctr1-SOD1$^{+/+}$. (mean±s.d. of at least four independent experiments, *P<0.05, two tailed t-tests). (FIG. 5G) Western blot indicating that protein levels of PTEN, NDFIP1 and NEDD4-2 are increased in SOD1$^{+/L144F}$ MN culture at day 14 after NF withdrawal. A-Tubulin was included as a loading control. Quantitative data is shown as fold change (FC) of ALS-SOD1$^{+/L144F}$ relative to Ctr1-SOD1$^{+/+}$. (mean±s.d., n=4 independent experiments, *P<0.05, two tailed t-tests). (FIG. 5H) Immunostaining to show subcellular localization of PTEN in FOXP1$^{on}$ ISL1$^{on}$ LMC-MNs at day 14 after NF withdrawal. Red dashed lines depict the borders of MN nuclei. Scale bar, 10 μm. Quantification of nucleus-to-cytosol ratios of PTEN average intensities (right panel) reveals elevated nuclear PTEN translocation in SOD1$^{+/L144F}$ LMC-MNs. (mean±s.d., n=4 independent experiments, *P<0.05, two tailed t-tests).

(FIG. 6A) Schematic illustration of experimental timeline. iPSCMN cultures at differentiation day 25 were subjected to overnight lentivirus (LV) infection to overexpress hsa-mir-17~92 or YFP as a control, followed by survival assay upon NF withdrawal from differentiation day 32. (FIGS. 6B and 6C) qPCR analysis of infected MN cultures at the survival assay end-point (–NF day 28). (FIG. 6B) Lentiviral transduction results in ectopic and sustained overexpression of hsa-mir-17~92. (FIG. 6C) Up-regulated PTEN, NDFIP1 and NEDD4-2 mRNA levels in stressed SOD1$^{+/L144F}$ iPSC~MNs are suppressed by overexpression of hsa-mir-17~92. Data is shown as fold change (FC) of each group relative to SOD1$^{+/L144F}$LV-YFP. (mean±s.d., n=4 independent experiments, *P<0.05, one-way ANOVA). (FIGS. 6D and 6E) Overexpression of hsa-mir-17~92 significantly increases SOD1$^{+/L144F}$ LMC-MN survival upon NF withdrawal. (FIG. 6D) LV-infected LMC-MNs before and after NF withdrawal, as revealed by SMI32 and FOXP1 immunostaining (FIG. 6E) LMC-MN survival rate was determined by quantification of LMC-MN (FOXP1$^{on}$ ISL1$^{on}$) numbers at day 28 of NF withdrawal and were normalized to LMC-MN numbers before NF withdrawal. (mean±s.d., n=4/5 independent experiments, *P<0.05, **P<0.01, one-way ANOVA).

(FIG. 7A) Genotypes of Ctrl and ALS mice, as well as the rescued ROSA26-loxp-STP-loxp (LSL)-mir-17~92 in SOD1$^{G93A}$ strain that overexpresses mir-17~92 in MNs by the Olig2$^{Cre/+}$ driver. (FIGS. 7B and 7C) Immunostaining and quantification of ChAT$^{on}$ MN numbers in sections of the lumbar hemi-ventral horn region at P100 reveals a significant restoration of SOD1$^{G93A}$ MN numbers. White dashed lines demarcate spinal cord margins. Scale bar, 50 μm. (n=4 mice, mean±s.d., *P<0.05, one-way ANOVA). (FIGS. 7D and 7E) Immunostaining and quantification of PTEN subcellular localization in hemi-ventral lateral ChAT$^{on}$ MNs of the lumbar spinal cord at P100. Nuclear PTEN accumulation in SOD1$^{G93A}$ MNs is reduced by mir-17~92 overexpression. High magnifications of the highlighted PTEN cells are shown in the right-most panels. White dashed lines depict MN nuclei. Scale bar is 10 μm. (mean±s.d., n=4 mice, *P<0.05, one-way ANOVA). (FIG. 7F) Roentgenograms of mice showing kyphosis phenotypes. Note that kyphosis is ameliorated in ALS; mir-17~92$^{MN-OE}$ mice. Red dotted lines depict hind limb shape; black dotted lines depict mouse spine. (FIG. 7G) Rotarod test for motor performance Latency to fall from an accelerating rotarod was determined and normalized to initial performance at P100 (as 100%). ALS; mir-17~92$^{MN-OE}$ mice display improved performance from P120. (mean±s.d., Ctrl (n=5), ALS (n=8), and ALS; mir-17~92$^{MN-OE}$ (n=6) mice, *P<0.05 for comparing ALS and ALS; mir-17~92$^{MN-OE}$ mice by two-way ANOVA). (FIG. 7H) KaplanMeier survival curves reflect the survival of Ctrl (n=32), ALS (n=33), and ALS; mir17~92$^{MN-OE}$ (n=22) mice. (****P<0.0001 for comparing ALS and ALS; mir-17~92$^{MN-OE}$ mice by log-rank Mantel-Cox test).

(FIG. 8A) Overview of the experimental strategy. Timeline shows the treatment schedule and stages for analyses. The schematic at left illustrates lumbar intrathecal injection (between L6 and S1) of scAAV9 expressing the primary transcript of mir-17~92 or GFP as a control. (FIG. 8B) In situ hybridization of miR-17 in a P100 lumbar spinal cord in SOD1$^{G93A}$ mice subjected to control scAAV9-GFP or scAAV9-mir-17~92 injection. Scale bar, 50 μm. (FIG. 8C) qPCR analysis reveals a significant increase in mir-17~92 expression in the whole lumbar spinal cords of SOD1$^{G93A}$ mice at P100 after scAAV9-mir-17~92 injection compared to that of scAAV9-GFP injected SOD1$^{G93A}$ mice. (mean±s.d., n=4, *P<0.05, two-tailed t-tests). (FIG. 8D) Neuromuscular function before and after scAAV9 injection, as assayed by evoked CMAPs in the GA muscle after stimulation of the sciatic nerve. The averages of maximum peak-to-peak CMAP values from each group of indicated age are plotted. The CMAP amplitude is already reduced in SOD1$^{G93A}$ mice at the time of scAAV9 injection and gradually reduces further over time, whereas overexpression of mir-17~92 significantly ameliorates neuromuscular function at P120 and P140. (mean±s.d., n=4-7 for each group, *P<0.05 for comparing scAAV9-mir-17~92 injected and scAAV9-GFP injected mice by two-way ANOVA). (FIG. 5E) The lifespans of SOD1$^{G93A}$ mice are prolonged by 14% following scAAV9 delivery of mir-17~92. KaplanMeier survival curves reflect the survival of Ctr1; AAV9-mir-17~92 (n=13), ALS; AAV9-GFP (n=15), and ALS; AAV9-mir-17~92 (n=17) mice. (***P<0.0005 for comparing ALS; AAV9-GFP and ALS; AAV9-mir-17~92 mice by log-rank Mantel-Cox test).

DETAILED DESCRIPTION OF THE INVENTION

Figure 1E:
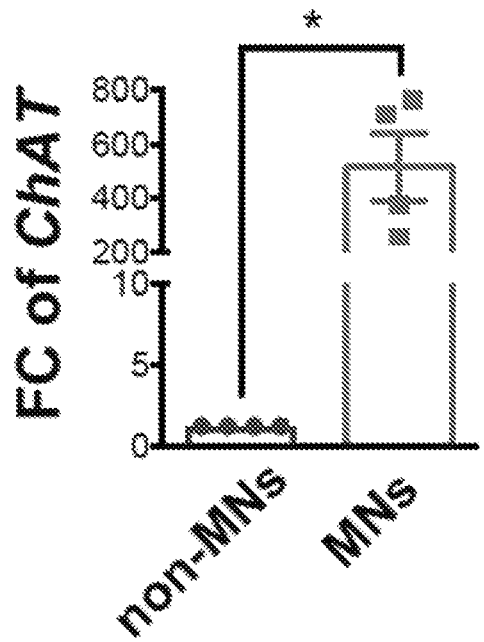

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs.

As used herein and in the appended claims, the singular forms "a," "an" and "the" include plural references unless the context clearly dictates otherwise.

As used herein interchangeably, the term a "miR gene product," "microRNA," "miRNA" or "miR" means a non-coding RNA between 18 and 25 nucleobases in length which hybridizes to and regulates the expression of a coding RNA.

As used herein, the terms "administration" and "administering" refer to the act of giving a drug, prodrug, or other agent, or therapeutic to a subject or in vivo, in vitro, or ex vivo cells, tissues, and organs.

As used herein, the term "at risk for developing" means a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent than required to be diagnosed with the condition or disease.

As used herein, the term "prevent the onset of" means to prevent the development of a condition or disease in a subject who is at risk for developing the disease or condition. In certain embodiments, a subject at risk for developing the disease or condition receives treatment similar to the treatment received by a subject who already has the disease or condition.

As used herein, the term "delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

In one aspect, the present disclosure provides a method of treating or preventing a motor neuron degeneration disease in a subject, comprising administering to the subject a therapeutically or prophylactically effective amount of one or more genes or transgenes containing members of mir-17~92.

In another aspect, the present disclosure provides a method of ameliorating motor deficits and prolonging lifespan of a subject with motor neuron degeneration disease, comprising administering to the subject an effective amount of one or more genes or transgenes containing members of mir-17~92.

In some embodiments, the administration of the invention comprises delivering one or more members of mir-17~92 cluster into central nervous system of the subject. In some embodiments, the one or more members of mir-17~92 cluster are delivered into spinal cord of the subject.

In some embodiments, the treatment or prevention of the motor neuron degeneration disease is through overexpression of the one or more members of mir-17~92 cluster in SOD1$_{G93A}$ MNs. In one embodiment, the overexpression of the one or more members of mir-17~92 cluster in SOD1$_{G93A}$ MNs causes a concomitant reduced expression of PTEN and the E3 ligases, Nedd4-2 and Ndfip1. In one embodiment, an early and selective down-regulation of mir-17~92 in SOD1$_{G93A}$ MNs precedes the onset of MN degeneration. Accordingly, mir-17~92/nPTEN manifests an MN-signature molecular change right before onset of MN degeneration in the SOD1$_{G93A}$ spinal cord. In one embodiment, selective mir-17~92/nPTEN dysregulation occurs early in SOD1$_{G93A}$ LMC MNs and may confer the MN subtype vulnerability to ALS disease.

In some embodiments, the method of the invention can delay or prevent the onset of MN degeneration or reduce the risk of developing MN degeneration.

A motor neuron disease (MND) is any of several neurodegenerative disorders that selectively affect motor neurons, the cells that control voluntary muscles of the body. In some embodiments, the motor neuron degeneration disease described in the present disclosure includes amyotrophic lateral sclerosis (ALS) and spinal muscular atrophies (SMA). In some embodiments, the ALS is familial ALS or sporadic ALS.

In some embodiments, the members of mir-17~92 cluster include, but are not limited to, miR-17, miR-17*, miR-18a, miR-19a, miR-19b, miR-20a, and miR-92a. In one embodiment, the member of mir-17~92 cluster is miR-17.

In some embodiments, the gene or transgene of the present disclosure is incorporated into or encapsulated in a carrier for administration or delivery. In some embodiments, the carrier is a viral vector or nanoparticle. In some embodiments, the viral vector is scAAV9, any serotypes of recombinant AAV (such as AAV1, AAV2, AAV9, AAV2/1, AAV2/5, AAV2/8, AAV2/9), or lentivirus. Any promoter capable of driving mir-17~92 cluster expression can be used in vector. In some embodiments, the promoter is H CMV, RSV, SV40, human 1-actin, hu ma. elongation factor-1α or cytomegalovirus early enhancer/chicken β-actin. In a certain embodiment, the transgene of the present disclosures comprises a CMV promoter and one more gene containing members of mir-17~92 cluster.

In some embodiments, the method of the invention further comprises administering one or more inhibitory nucleic acids targeting SOD1, a transgene encoding a nuclear PTEN interfering peptide, an ER stress inhibitor, a stress granule blocker or a miRNA biogenesis activator.

Inhibitory nucleic acids used in the present methods include antisense oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target SOD1. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

For example, antisense oligonucleotides are typically designed to block expression of a DNA or RNA target by binding to the target and halting expression at the level of transcription, translation, or splicing. Antisense oligonucleotides of the present disclosure are complementary nucleic acid sequences designed to hybridize under stringent conditions to SOD1.

For example, the inhibitory nucleic acids used in the methods described herein comprise one or more modified bonds or bases. Modified bases include phosphorothioate, methylphosphonate, peptide nucleic acids, or locked nucleic acid (LNA) molecules.

Preferably, the modified nucleotides are locked nucleic acid molecules, including alpha-L-LNAs. LNAs comprise ribonucleic acid analogues wherein the ribose ring is "locked" by a methylene bridge between the 2'-oxgygen and the 4'-carbon; i.e., oligonucleotides containing at least one LNA monomer.

For example, the nucleic acid sequence that is complementary to SOD1 can be an interfering RNA, including but not limited to a small interfering RNA ("siRNA") or a small hairpin RNA ("shRNA"). Methods for constructing interfering RNAs are well known in the art.

The gene of the present disclosure or the agent described herein for in combination with the gene can be formulated as pharmaceutical compositions or combinations with a pharmaceutically acceptable carrier. The pharmaceutical compositions or combinations can be formulated to be administered parenterally, topically, orally, intrathecally or by local administration. The pharmaceutical compositions or combinations can be formulated in any way and can be administered in a variety of unit dosage forms depending upon the condition or disease and the degree of illness, the general medical condition of each patient, the resulting preferred method of administration and the like. In one embodiment, the pharmaceutical composition or combination can be administered intrathecally. For example, in embodiments, the pharmaceutical composition or combination can be administered in vivo via intrathecal injection.

Pharmaceutical compositions or combinations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

In some embodiments, the methods described herein can include co-administration with one or more inhibitory nucleic acids targeting SOD1, a transgene encoding a nuclear PTEN interfering peptide, an ER stress inhibitor, a stress granule blocker or a miRNA biogenesis activator.

In another aspect, the present disclosure provides a method of screening a drug protecting motor neuron subtypes in ALS in vitro, comprising (i) providing a stem cell line harboring a transgene comprising a fALS gene and a reporter gene, (ii) culturing a drug with the cell line; (iii) directing differentiation of the cell to the motor neuron cells and expression; and (iv) determining the said drug is effective to protect motor neuron subtypes in ALS if a motor neuron subtype is generated from the stem cell line.

In some embodiments, the stem cell line is an embryonic stem cell line or iPSC cell line. In some embodiments, the stem cell line is human or mouse stem cell line.

In some embodiments, the fALS gene is C9orf72 mutation containing expanded GGGGCC repeats, FUS-R521C, FUS-P525R, FUS-R521H, FUS-Q210H, FUS-R514G, FUS-C1574G, SOD1-G93A, SOD1-A4V, SOD1-D90A, SOD1-D91A, SOD1-H46R, SOD1-A89V, SOD1-I113T, TDP43-A315T, TDP43-Q343R, TDP43-M337V, TDP43-N345K, TDP43-I383V or TDP43-M337V.

In some embodiments, the reporter is a double reporter. In some embodiments, the double reporter is Hb9::RFP and FoxP1::GFP.

In a further aspect, the present disclosure provides a method for diagnosis of motor neuron subtypes in ALS in a subject, comprising providing a biological sample and detecting the presence of one or more members of mir-17~92 cluster or nuclear PTEN, wherein the presence of dysregulated mir-17~92 members or nuclear PTEN is indicative of a diagnosis of motor neuron subtypes in ALS or a susceptibility to motor neuron subtypes in ALS in the subject.

Also provided herein are kits for use in diagnosing motor neuron subtypes in ALS or susceptibility to motor neuron subtypes in ALS in a subject, comprising one or more reagents for detecting the presence of one or more members of mir-17~92 cluster or PTEN in a biological sample. In a particular embodiment, the kit comprises at least one contiguous nucleotide sequence that is substantially or complementary to one or more members of mir-17~92 cluster or PTEN for detecting the presence of one or more members of mir-17~92 cluster or PTEN. For example, the nucleic acids can comprise at least one sequence which is complementary (completely, partially) to mir-17~92 or PTEN. In one embodiment, the one or more reagents in the kit are labeled, and thus, the kits can further comprise agents capable of detecting the label. The kit can further comprise instructions for detecting motor neuron subtypes in ALS using the components of the kit.

The invention is further described in the following examples, which do not limit the scope of the invention described in the claims.

EXAMPLES

Materials and Methods

Mice

Mice carrying the mutant human SOD1$_{G93A}$ transgene (B6SJL-Tg(SOD1*G93A)1Gur/J) were purchased from Jackson Laboratory. The motor neuron-specific mir17~92-overexpressing mice, Olig2$_{Cre/+}$; ROSA26-loxp-STOP-loxp-mir-17~92$_{f/f}$ (mir-17~92$_{MN-OE}$), were generated previously (20), and were further crossed with SOD1$_{G93A/+}$; ROSA26-loxp-STOP-loxp-mir-17~92$_{f/f}$ mice to obtain SOD1$_{G93A}$; Olig2$_{Cre/+}$; ROSA26-loxp-STOP-loxp-mir-17~92$_{f/f\ or\ f/+}$ (ALS; mir-17~92$_{MN-OE}$) rescue mice. For all experiments, ALS; mir-17~92$_{MN-OE}$ mice were compared with their SOD1$_{G93A}$; Olig2$_{Cre/+}$ or SOD1$_{G93A}$; ROSA26-loxp-STOP-loxp-mir-17~92$_{f/+\ or\ f/f}$ ALS littermates.

To generate mice with double transgenic (Tg) reporters, the spinal MN reporter Hb9::RFP construct was electroporated into BALB/c embryonic stem cells (ESCs), and injected into the host mouse. Several chimeric mice were born and we further crossed them to C57BL/6J wild type mice to obtain the germ line-transmitted transgenic Hb9::RFP founder lines. The FoxP1::GFP ES cell line that harbors a BAC with ~195 kb of the 5' FoxP1 sequence and GFP inserted at the initiating codon (a kind gift from Jeremy Dasen and Hynek Wichterle) (44) was used to derive the FoxP1::GFP mouse strain in a C57BL/6 background. We then mated the FoxP1::GFP line to the Hb9::RFP line to get mice with double Tg reporters (FoxP1::GFP; Hb9::RFP) in the C57BL/6 background. Double Tg FoxP1::GFP; Hb9::RFP embryos were analyzed at E12.5 to validate the efficacy of the double reporters. All of the live animals were kept in an SPF animal facility, approved and overseen by IACUC Academia Sinica.

Tissue Collection

Mice were sacrificed under anesthetic with 300 μL of 20 mg/mL Avertin (2,2,2-Tribromoethanol, Sigma) and subsequently perfused with PBS and 4% paraformaldehyde (PFA) in PBS. Whole spinal cords were isolated, refixed and sucrose cryoprotected. Spinal cords were embedded in FSC 22 frozen section media (Leica), and cut into 10 μm cryostat sections, which were then subjected to immunostaining or in situ hybridization by 3' DIG-labeled LNA miRCURY probes (Exiqon).

Laser Capture Microdissection

Mice were sacrificed under anesthetic with Avertin and subsequently perfused by DEPC-PBS. The spinal cord was removed and dissected into several segments within 7 min, followed by embedding in FSC 22 frozen section media (Leica). The frozen blocks were cryosectioned at −20° C. into 20 μm-thick slices and stored at −80° C. until the laser capture procedure.

For the staining of MNs, each slice was washed by RNase-free 70% ethanol for 60 seconds, stained with 1% Azure B (MP Biomedicals) in washing solution for 180 seconds, followed by another 20 seconds-wash, and then air-dried completely. MNs were identified as large, darkly-stained cell bodies residing in the ventral lateral region of the L5 lumbar spinal cord, whereas dorsal non-MNs were identified as Azure B-stained cell bodies located in the dorsal spinal cord. Around 400~500 MNs or dorsal non-MNs were microdissected (PALM MicroBeam, ZEISS, 20× objective) from each mouse and collected into a single tube. MNs and dorsal non-MNs from 3~4 mice per strain were collected.

Spinal Motor Neuron Counts

At each indicated stage, ChAT$_{on}$ MNs in the L5 ventral horns with DAPI were counted on one side of a 10 μm sectioned spinal cord. MNs that did not show regular nuclear shapes were excluded. The histograms represent the average MN counts from at least 3 sections per mouse (n≥3 mice) of the same age and genotype.

AAV9 Virus Preparation and Injection

AAV9-mir-17~92 and AAV9-GFP were packaged by the AAV Core Facility in Academia Sinica. For intrathecal injection, mice at P60 were anesthetized by isoflurane. The lumbar spinal cord was exposed through a ~1.5 cm window surgically cut on the back of the mice. 20 μL of either AAV9-GFP or AAV9-mir-17~92 (5×10$^9$ vg/μL) was injected at a rate of 4 μL/min into the groove between the L6 and S1 segments using a 27 G needle. A flick of the mouse's tail indicated successful injection.

Example 1 mir17~92/PTEN is Expressed in Adult Spinal MNs and Requirement of mir-17~92 to Maintain MN Survival We discovered in a previous study (Tung, Y. T., Lu, Y. L., Peng, K. C., Yen, Y. P., Chang, M., Li, J., Jung, H., Thams, S., Huang, Y. P., Hung, J. H., et al. (2015). Mir-17~92 Governs Motor Neuron Subtype Survival by Mediating Nuclear PTEN. Cell reports 11, 1305-1318) that expression of the mir-17~92 miRNA cluster is enriched in developing LMC-MNs, and the cluster functions to promote the survival of LMC-MNs before they reach the innervating muscles from which they receive neurotrophic support. Mechanistically, mir-17~92 targets PTEN and its associated E3 ubiquitin ligase complex, i.e., Nedd4-2 and Ndfip1. As a consequence, PTEN is less mono-ubiquitinated and mostly remains in the cytoplasm to prevent LMC-MNs undergoing naturally-occurring apoptosis in the developing spinal cord (FIG. 1A).

Given that many spinal onset ALS patients start with limb weakness and that active denervation occurs more prominently in the limbs of ALS patients than in their thoracic paraspinal muscles, LMC-MNs appear to be more susceptible to undergoing degeneration compared to other MN types in ALS (Kanning, K. C., Kaplan, A., and Henderson, C. E. (2010). Motor neuron diversity in development and disease. Annual review of neuroscience 33, 409-440). This manifestation prompted us to examine if mir-17~92/nuclear PTEN (nPTEN) could account for the differential vulnerability of MN subtypes in ALS through its differential expression in adult MN subtypes (FIG. 1A).

We firstly checked whether the expression of mir-17~92 remains enriched in adult spinal MNs by in situ hybridization (ISH) together with immunostaining in sectioned adult lumbar spinal cord at postnatal day 40 (P40), using miR-17 as the representative miRNA in the cluster and choline acetyltransferase (ChAT) as an MN marker (FIG. 1B). Although miR-17 expression was detectable in neurons in the whole spinal cord, its expression was more prominent in the ventral lateral spinal cord (FIG. 1B). Quantification verified that the expression level of miR-17 in spinal MNs was higher compared to Renshaw cells (RCs) locating at the ventral spinal cord.

Figure 1F:
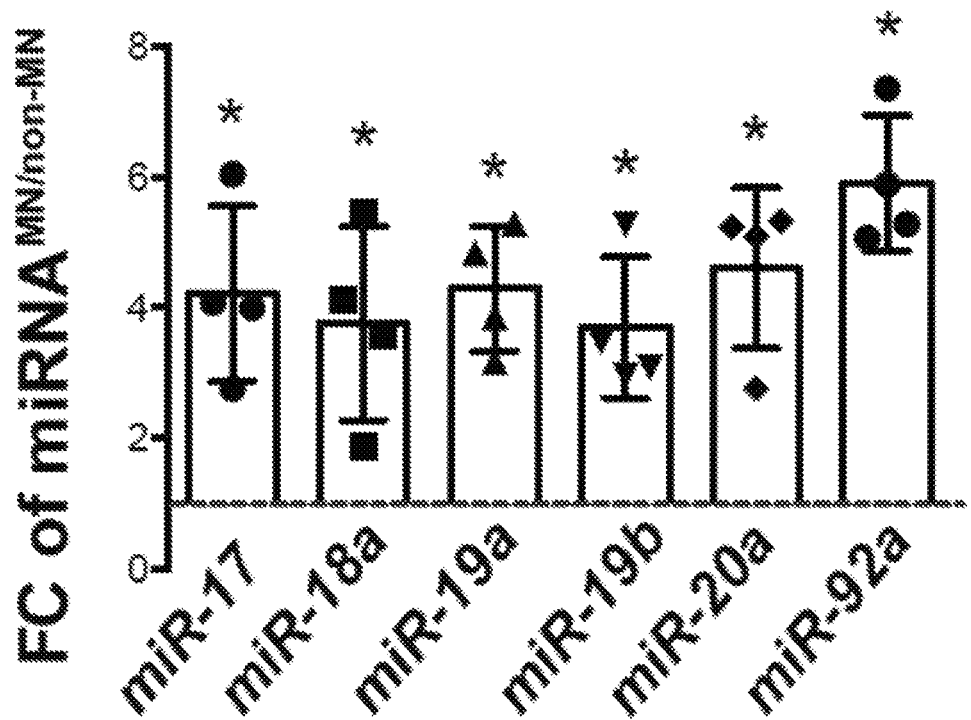

To corroborate the enrichment of each member of the mir-17~92 cluster in MNs, we laser microdissected the cell bodies of ventral lateral MNs and non-MNs from dorsal spinal cords (FIGS. 1C and 1D) and performed quantitative RT-PCR (qPCR). ChAT was used to ensure that we captured bona fide MNs (FIG. 1E). Compared to non-MNs from dorsal spinal cord, the expression of mir-17~92 was more abundant in MNs of adult mouse spinal cord (FIG. 1F), supporting that mir-17~92 expression is enriched and sustained from developing embryos to adult spinal MNs.

Next, we examined the expression of the target of mir-17~92 (i.e., PTEN) in adult spinal cord. Interestingly, PTEN was abundantly expressed in ventral-lateral ChAT$^{on}$ MNs and was predominantly localized in the cytosol, whereas expression of PTEN in dorsal cells and Calbindin$^{on}$ RCs was nearly undetectable. These results indicate that in the adult spinal cord, PTEN is expressed preferentially in the spinal MNs and exhibits a discriminatory cytosolic localization, possibly a reflection of the enrichment of mir-17~92 expression.

Figure 1G:
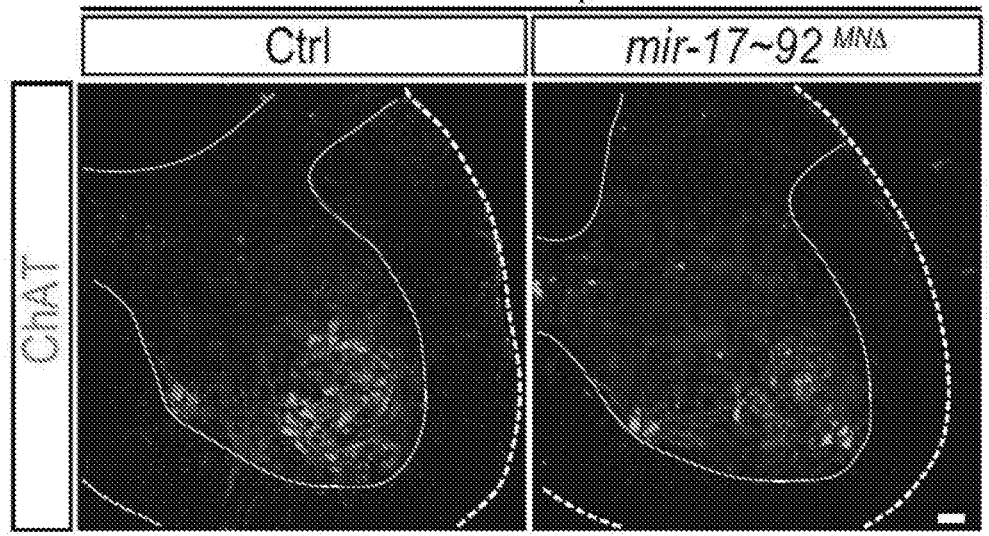
Figure 1H:
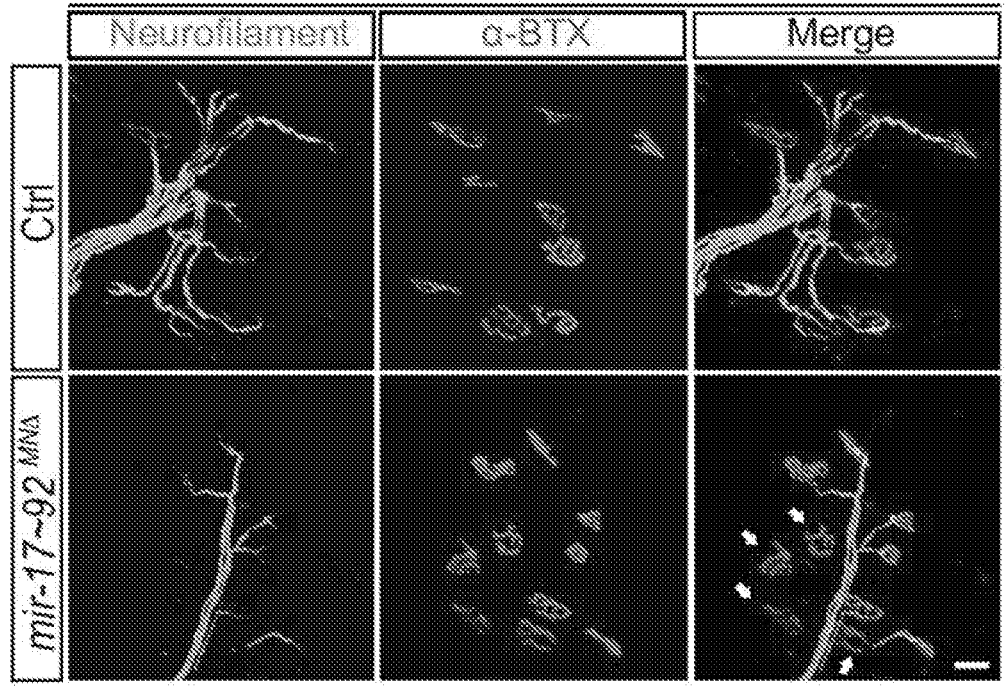
Figure 1I:
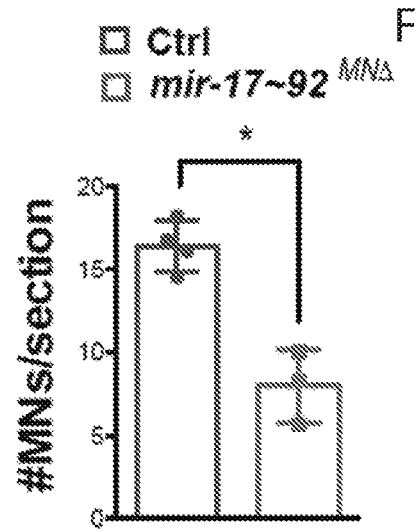
Figure 1J:
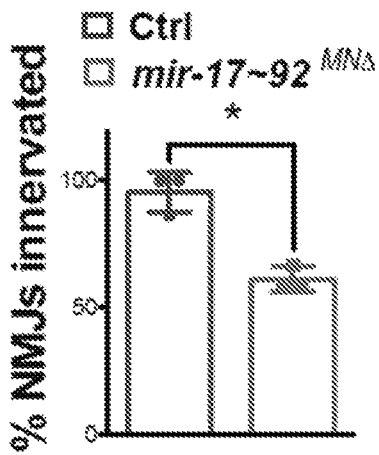
Figure 1K:
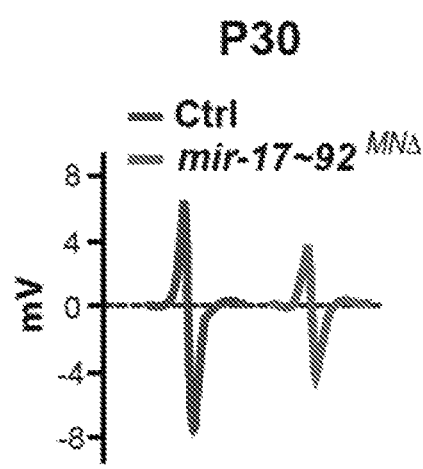

Our previous study indicated that mir-17~92 deletion in MNs (Olig2$^{Cre/+}$: mir-17~92 foxed=mir-17~92$^{MNΔ}$) led to specific loss of LMC-MNs at embryonic stage E12.5~13.5 (Tung, Y. T., Lu, Y. L., Peng, K. C., Yen, Y. P., Chang, M., Li, J., Jung, H., Thams, S., Huang, Y. P., Hung, J. H., et al. (2015). Mir-17~92 Governs Motor Neuron Subtype Survival by Mediating Nuclear PTEN. Cell reports 11, 1305-1318). Consequently, ~70% of the mir-17~92$^{MNΔ}$ embryos died as neonates, possibly due to the severe movement defects (N=69). The remainder of the surviving mir-17~92$^{MNΔ}$ mice allowed us to assess the MN phenotype at later stages after birth. Among these mutants (N=17), ~85% exhibited smaller size and reduced body weight. Nearly all mir-17~92$^{MNΔ}$ mice displayed some hallmarks of "ALS" pathologies, including that 1) ChAT$^{on}$ MN numbers were significantly reduced in the spinal cords of the mir-17~92$^{MNΔ}$ mice at P30 (FIG. 1G and quantification in 1I). 2). Remarkably, no denervation was detected at P30 in the gastrocnemius (GA) muscle of the control mice, whereas the mir-17~92$^{MNΔ}$ mice manifested drastic denervation of motor endplates (FIG. 1H and quantification in 1J). 3). The compound muscle action potential (CMAP) in mir-17~92$^{MNΔ}$ mice was reduced by ~35% relative to control values (FIG. 1K). Taken all together, our analyses indicate that mir-17~92/PTEN is highly expressed in adult spinal MNs and the down-regulation of mir-17~92 in MNs is sufficient to cause adult MN loss.

Figure 2A:
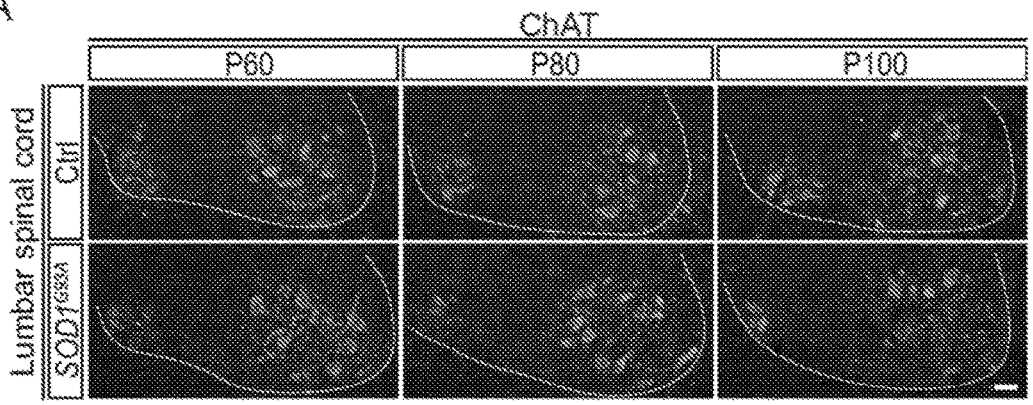
FIGS. 2A to 2J show dysregulation of mir-17~92/nPTEN in presymptomatic SOD1$^{G93A}$ MNs.
Figure 2B:
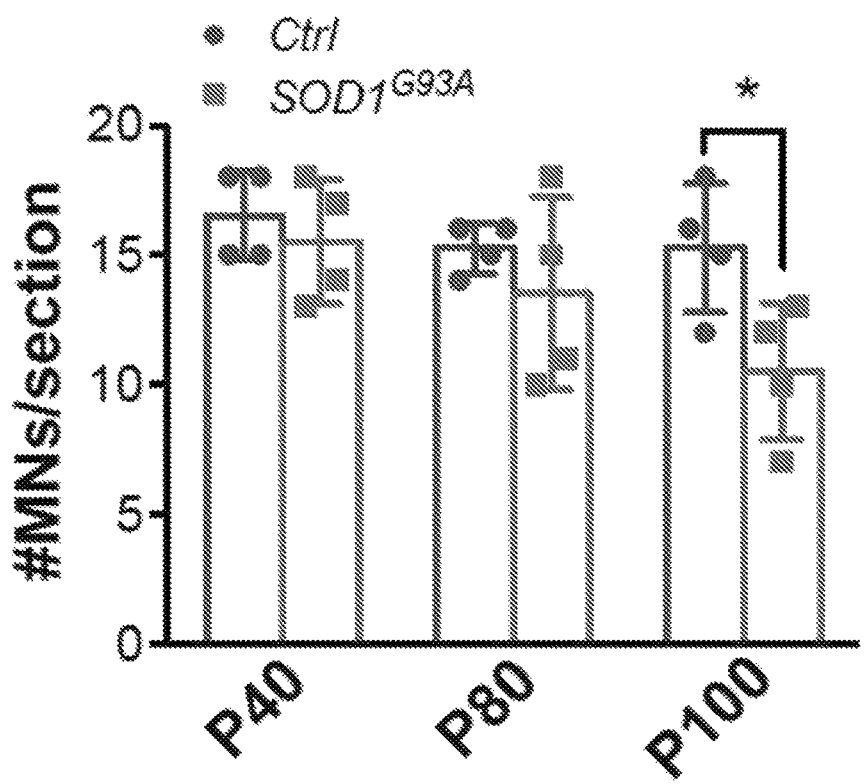
Figure 2C:
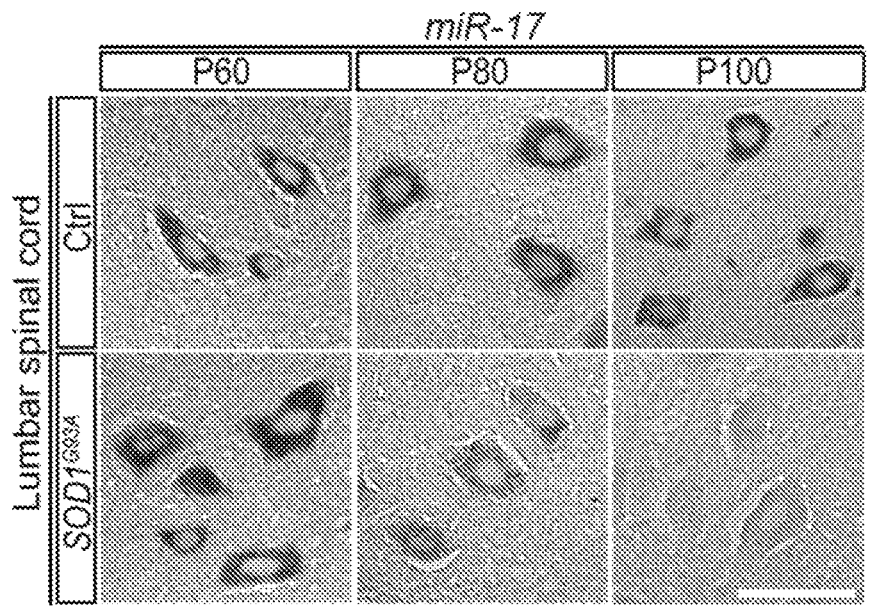
Figure 2D:
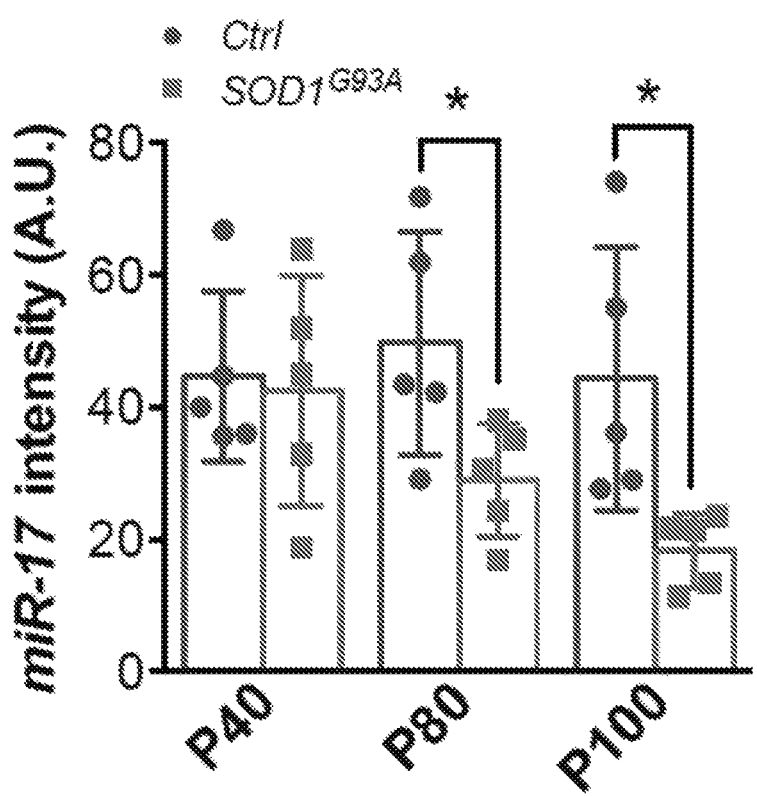

Example 2 Early Presymptomatic Dysregulation of mir-17~92InPTEN Axis in MNs of SOD1$^{G93A}$ Mice To test the hypothesis that dysregulation of mir-17~92/nPTEN pathway is involved in MN degeneration of ALS, we used SOD1$^{G93A}$ mouse model as a paradigm. Throughout adulthood, numbers of ChAT$^{on}$ MNs remained unaffected in SOD1$^{G93A}$ lumbar spinal cords before P80 and were slightly reduced at P100 (FIG. 2A, quantification in 2B). Even with comparable MN numbers between Ctrl and SOD1$^{G93A}$ mice at P80, we already observed a significant down-regulation of miR-17 expression in SOD1$^{G93A}$ MNs (FIG. 2C, quantification in 2D). The down-regulation trend appeared more prominently in MNs as miR-17 expression remained low and comparable in both dorsal Tuj1$^{on}$ interneurons (dINs, resistant to ALS) and calbindiel$^{on}$ RCs (intact in presymptomatic ALS stages) (Wootz, H., Fitzsimons-Kantamneni, E., Larhammar, M., Rotterman, T. M., Enjin, A., Patra, K., Andre, E., Van Zundert, B., Kullander, K., and Alvarez, F. J. (2013). Alterations in the motor neuron-renshaw cell circuit in the Sod1(G93A) mouse model. J Comp Neurol 521, 1449-1469) throughout the indicated ages between both Ctrl and SOD1$^{G93A}$ mice.

Figure 2E:
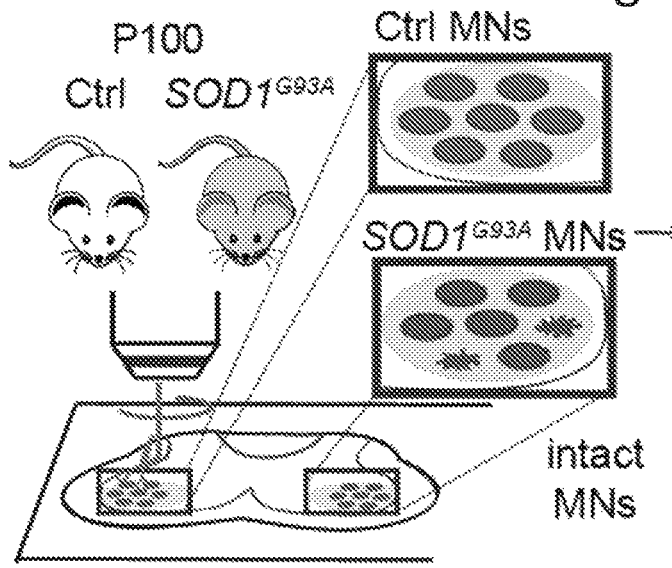
Figure 2F:
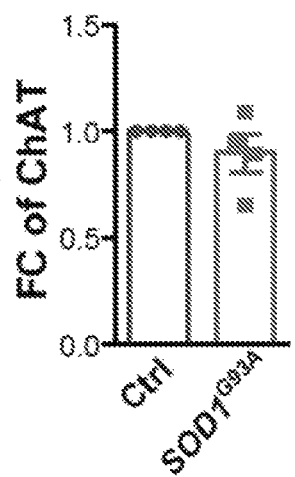
Figure 2G:
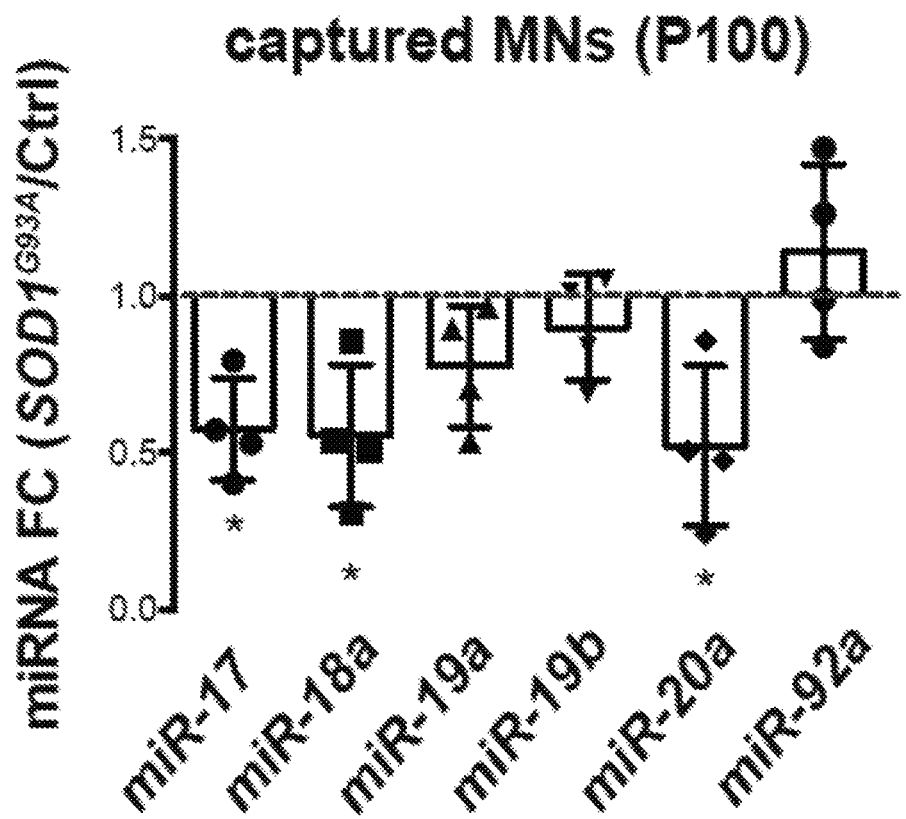

To precisely quantify the expression of miR-17 and other members of mir-17~92 cluster in intact SOD1$^{G93A}$ lateral MNs before degeneration, we used laser microdissection to collect MNs with healthy morphology in the lateral ventral spinal cord based on their size and shape (see STAR Methods for details), from both Ctrl and SOD1$^{G93A}$ mice at P100 (FIG. 2E) and compared mRNA/miRNA expression by qPCR. While the expression of ChAT was unchanged between the microdissected control and SOD1$^{G93A}$ MNs (FIG. 2F), several members of mir-17~92 had already manifested significantly declined expression in SOD1$^{G93A}$ MNs (FIG. 2G). These data reflected that mir-17~92 expression is down-regulated prior to onset of MN death in SOD1$^{G93A}$ MNs.

Figure 2H:
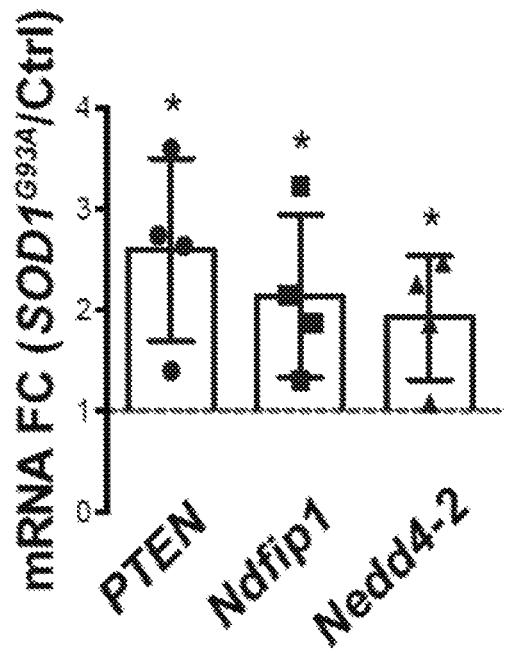
Figure 2I:
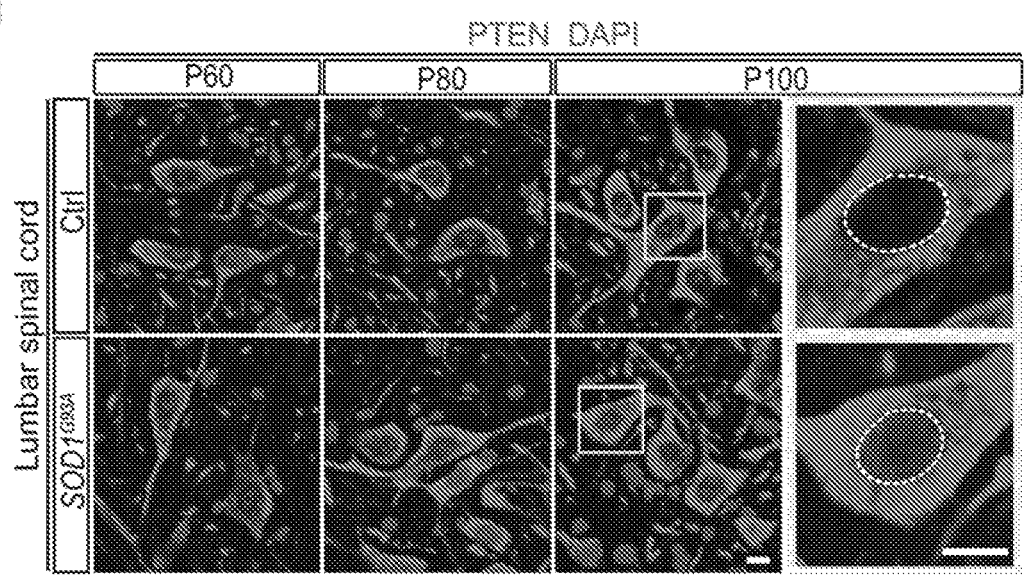
Figure 2J:
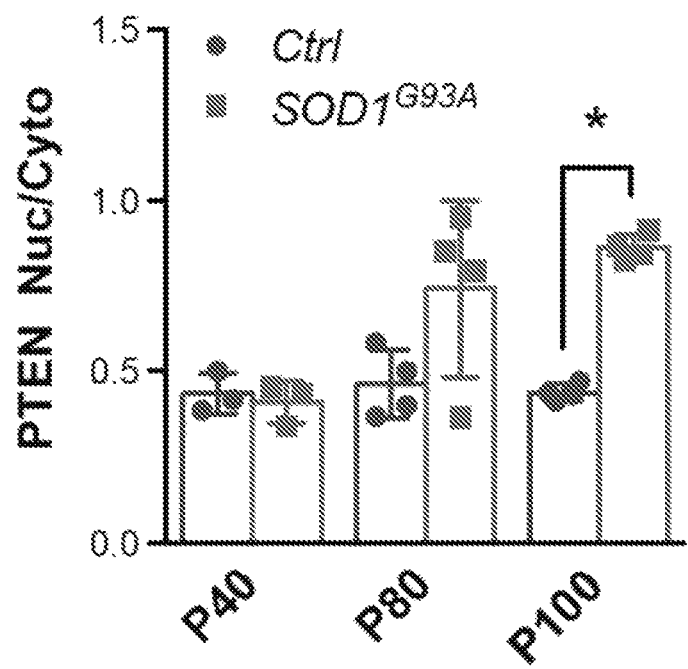

Moreover, along with the down-regulation of mir-17~92 in the same sets of microdissected MNs, we observed a concomitant increase in the expression of its targets PTEN, Nedd4-2 and Ndfip1 in captured SOD1$^{G93A}$ MNs at P100 when compared to controls (FIG. 2H). As Nedd4-2/Ndfip1 promote PTEN mono-ubiquitination to facilitate its nuclear import (Tung et al., 2015), we next analyzed subcellular PTEN localization in MNs from control and SOD1$^{G93A}$ mice at P40, P80 and P100. In SOD1$^{G93A}$ MNs at P100, the intensity of PTEN increased significantly in the whole cell (PTEN$^{total}$), as well as in the nucleus (PTEN$^{nucleus}$) (FIG. 2I). Additionally, we also observed a dramatically elevated ratio of PTEN$^{nucleus/cytosol}$ in SOD1$^{G93A}$ MNs (FIG. 2J), indicating that the elevated PTEN tended to accumulate in the MN nuclei. The delay until significant nuclear PTEN accumulation (P100) upon mir-17~92 reduction (P80) might reflect the time required for coupling of PTEN post-transcriptional regulation and post-translational modification. In contrast to ChAT$^{on}$ ventral lateral MNs, PTEN expression in control, SOD1$^{G93A}$ Calbindin$^{on}$ RCs and Tuj1$^{on}$ dINs remained nearly undetectable at all ages (data not shown). Collectively, the data demonstrates that disruption of the mir-17~92/nPTEN pathway is a signature event in spinal MNs before the onset of MN loss in the SOD1$^{G93A}$ spinal cord.

Example 3 Selective Dysregulation of mir-17~92 in SOD1$^{G93A}$ LMC-MNs

To further examine if mir-17~92 dysregulation contributes to the vulnerability of limb-innervating MNs to ALS, in this scenario, we established a novel double transgenic mouse strain in which limb-innervating LMC-MNs are labeled with GFP (Foxp1::GFP) and generic motor neurons are labeled with RFP (Hb9::RFP). To verify the fidelity of the reporter, we examined the expression pattern of the double fluorescence reporters along the rostrocaudal axis of the spinal cord. As expected, Foxp1::GFP signal was detected in LMC-MNs, whereas Hb9::RFP signal was detected in both LMC-MNs and non-LMC-MNs. Accordingly, LMC-MNs and non-LMC-MNs could be distinguished by a combination of the transgenic reporters in vivo, with GFP$^{on}$/RFP$^{on}$ representing LMC-MNs and GFP$^{off}$/RFP$^{on}$ representing non-LMC-MNs. However, Foxp1::GFP became less specifically expressed in LMN-MNs and was expressed in some spinal INs. Moreover, Hb9::RFP was also restricted to subsets of adult MNs (data not shown). Consequently, we adopted an alternative embryonic stem cell (ESC) differentiation approach by taking advantages of the fact that: 1) high-fidelity transgenic reporters are available to delineate MN subtypes; 2) conditions for deriving MN subtypes with authentic rostrocaudal spinal identities are well established (Davis-Dusenbery, B. N., Williams, L. A., Klim, J. R., and Eggan, K. (2014). How to make spinal motor neurons. Development 141, 491-501 Davis-Dusenbery et al., 2014); 3) postmitotic MN subtypes can be FACS-collected with a dual reporter system; and 4) conditions for maturing and accelerating MN degeneration in vitro are well defined (Thams, S., Lowry, E. R., Larraufie, M. H., Spiller, K. J., Li, H., Williams, D. J., Hoang, P., Jiang, E., Williams, L. A., Sandoe, J., et al. (2018). A Stem Cell-Based Screening Platform Identifies Compounds that Desensitize Motor Neurons to Endoplasmic Reticulum Stress. Molecular therapy: the journal of the American Society of Gene Therapy).

In this scenario, we further derived Foxp1::GFP; Hb9::RFP embryonic stem cell (ESC) line and then differentiated them into spinal MNs using a defined protocol that generates cervical/brachial Hoxa5$^{on}$ MNs (composed of 15% LMC-MNs and 85% non-LMC-MNs). Immunostaining of ESC-derived MNs revealed that Hb9::RFP cells are co-expressed with the generic MN markers Isl1/2 and Hb9, whereas Foxp1::GFP cells were manifested with the LMC-MN identity as Foxp1$^{on}$/Lhx3$^{off}$. This outcome was further validated by qPCR analysis from FACS-purified GFP$^{on}$/RFP$^{on}$ cells, which exhibited high Raldh2 and Foxp1 expression, but low expression of Lhx3. Above all, our double reporter system provides an ideal platform to study LMC-MN versus non-LMC-MN phenotypes in a well-defined differentiation system.

Figure 3A:
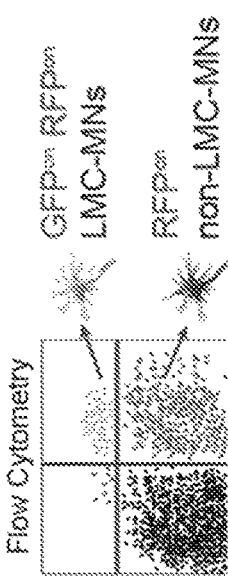
FIGS. 3A to 3G show that SOD1$_{G93A}$ LMC-MNs are more susceptible to degeneration and exhibit early reduction of mir-17~92.
Figure 3B:
Figure 3B:
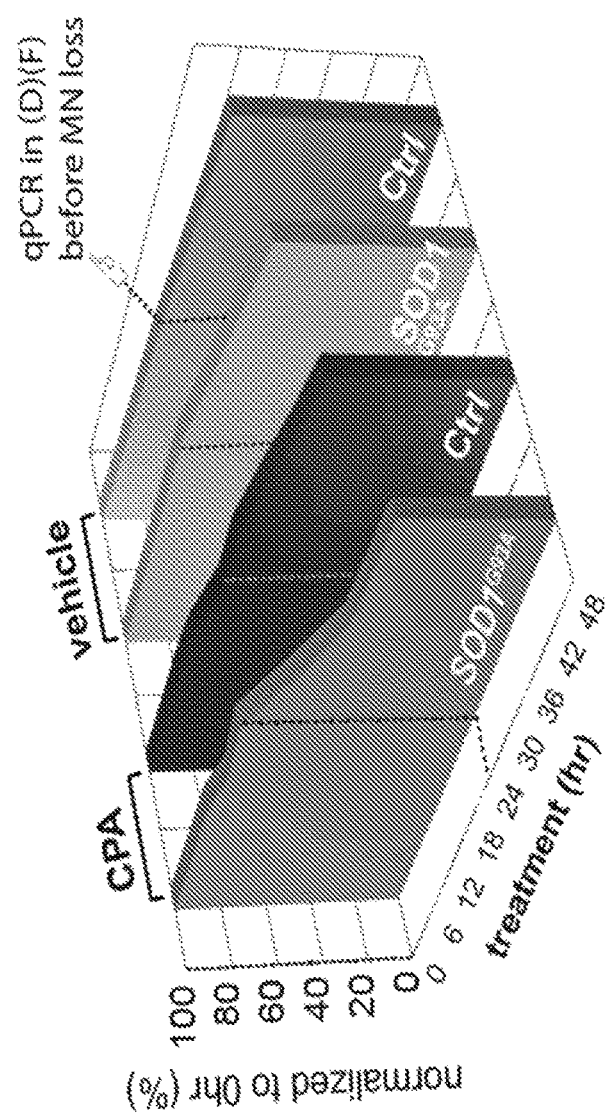
Figure 3C:
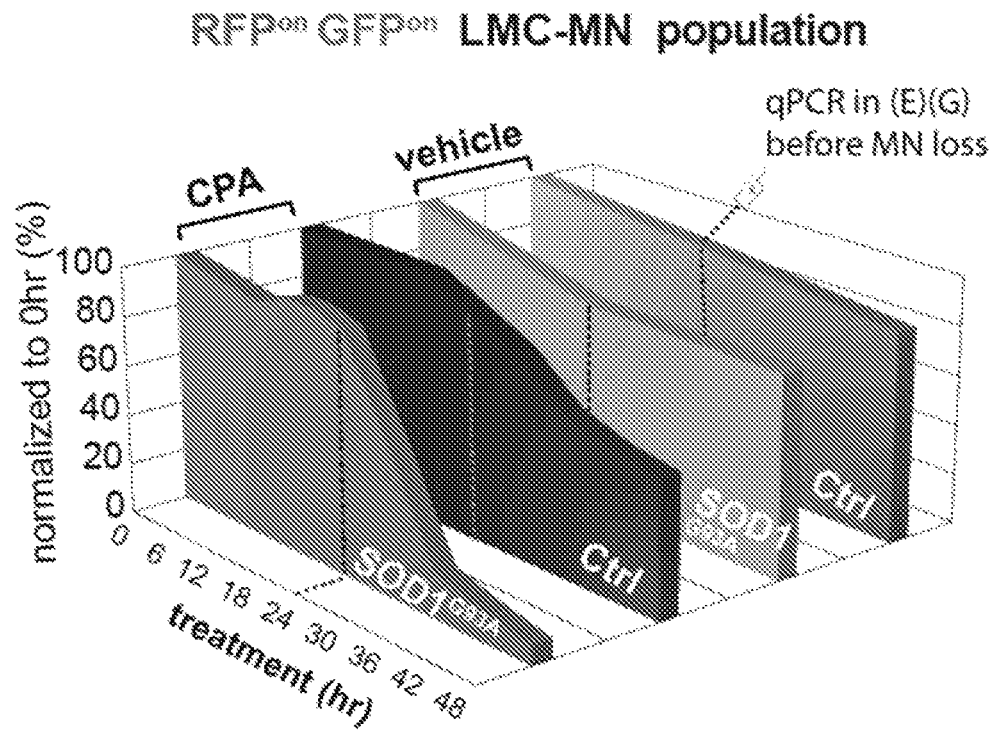

Next, we crossed the Foxp1::GFP; Hb9::RFP strain to Ctrl and SOD1$^{G93A}$ mice to get the Ctrl and SOD1$^{G93A}$ double reporter ESC lines, then harnessed them into MN subtypes (FIG. 3A). In the absence of stress conditions upon differentiation, both Ctrl and SOD1$^{G93A}$ lines could be differentiated into comparable LMC-MNs and non-LMC-MNs with no preferential cell loss. The expression levels of mir-17~92 members were also similar between Ctrl and SOD1$^{G93A}$ lines in the basal condition. To accelerate ALS disease progression in vitro, we applied cyclopiazonic acid (CPA) to Ctrl and SOD1$^{G93A}$ ESC-derived MNs. In a recent study that applied the same ESC differentiation approach used here (Thams, S., Lowry, E. R., Larraufie, M. H., Spiller, K. J., Li, H., Williams, D. J., Hoang, P., Jiang, E., Williams, L. A., Sandoe, J., et al. (2018). A Stem Cell-Based Screening Platform Identifies Compounds that Desensitize Motor Neurons to Endoplasmic Reticulum Stress. Molecular therapy: the journal of the American Society of Gene Therapy), CPA was demonstrated to be an endoplasmic reticulum stressor that exhibited preferential toxicity to MNs and only mild effects on INs. Upon CPA stress, we found that non-LMC-MN populations were more resistant to the ER stressor in both Ctrl and SOD1$^{G93A}$ MNs. In contrast, SOD1$^{G93A}$ LMC-MNs exhibited drastic cell loss after 24-48 hours of CPA treatment compared to Ctrl LMC-MNs (FIGS. 3B and 3C). Notably, no differential degeneration was displayed between Ctrl and SOD1$^{G93A}$ ESC-derived MNs when treated with vehicle (DMSO) alone (FIGS. 3B and 3C). Thus, using our newly established ALS double reporter system, we could capture the differential degrees of degeneration among MN subtypes under CPA treatment.

Figure 3D:
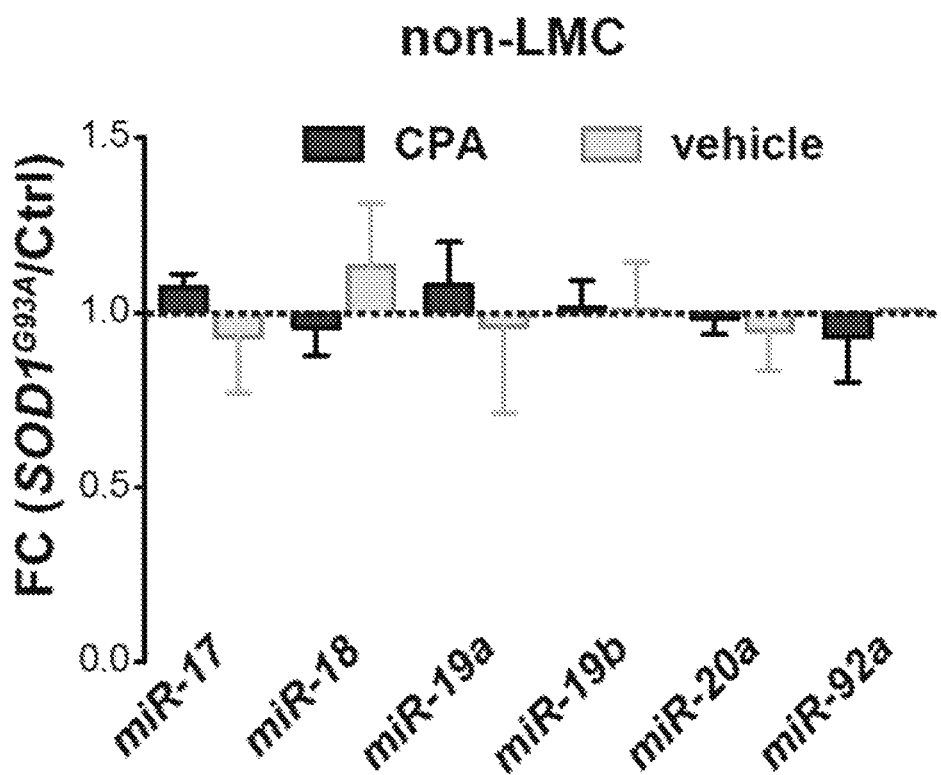
Figure 3E:
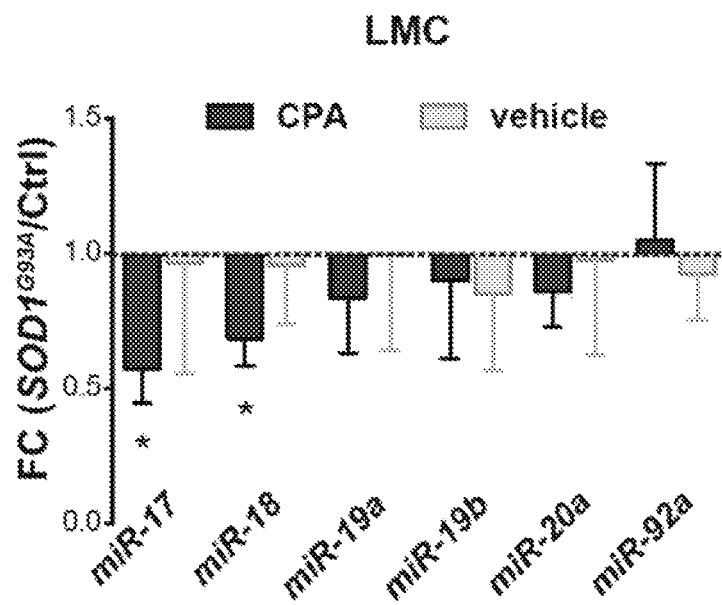
Figure 3F:
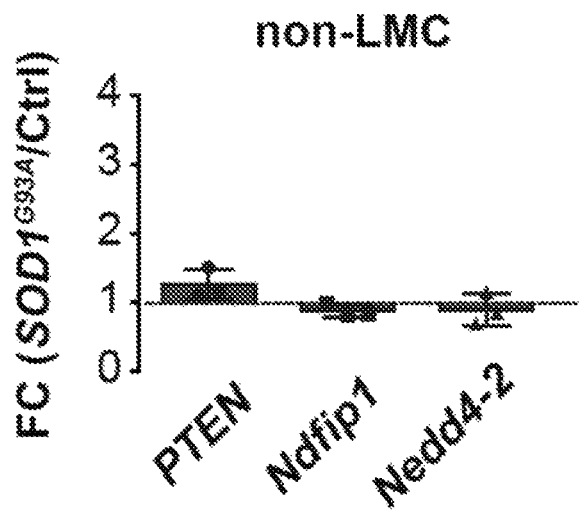
Figure 3G:
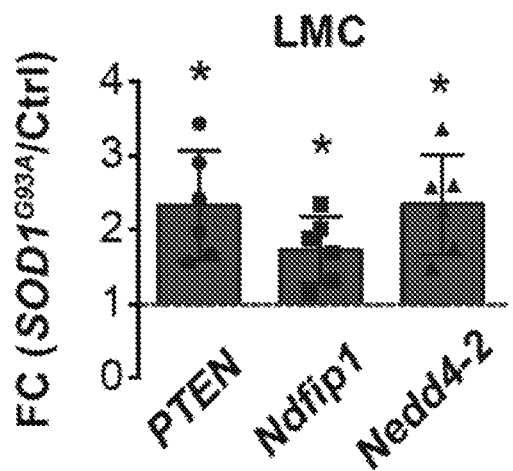

To elucidate the differential sensitivity to CPA stress in MN subtypes, we investigated the expression of mir-17~92 and its targets (PTEN, Ndfip1 and Nedd4-2) in our ESC-derived MN system at 24 hours post-CPA treatment (i.e. at a time-point prior to LMC-MN loss). In SOD1$^{G93A}$ LMC-MNs, we observed a trend of down-regulation of mir-17~92 members, whereas there was no significant difference being observed between Ctrl and SOD1$^{G93A}$ non-LMC-MNs (FIGS. 3D and 3E). Concomitantly, expressions of the mir-17~92 targets (PTEN, Ndfip1 and Nedd4-2) were also specifically up-regulated in SOD1$^{G93A}$ LMC-MNs (FIGS. 3F and 3G). Above all, SOD1$^{G93A}$ LMC-MNs are more prone to undergoing degeneration upon stress, with a selective manifestation of mir-17~92 downregulation.

Example 4 SOD1$_{G93A}$ LMC-MNs are More Prone to mir-17~92/nPTEN Dysregulation

Figure 4A:
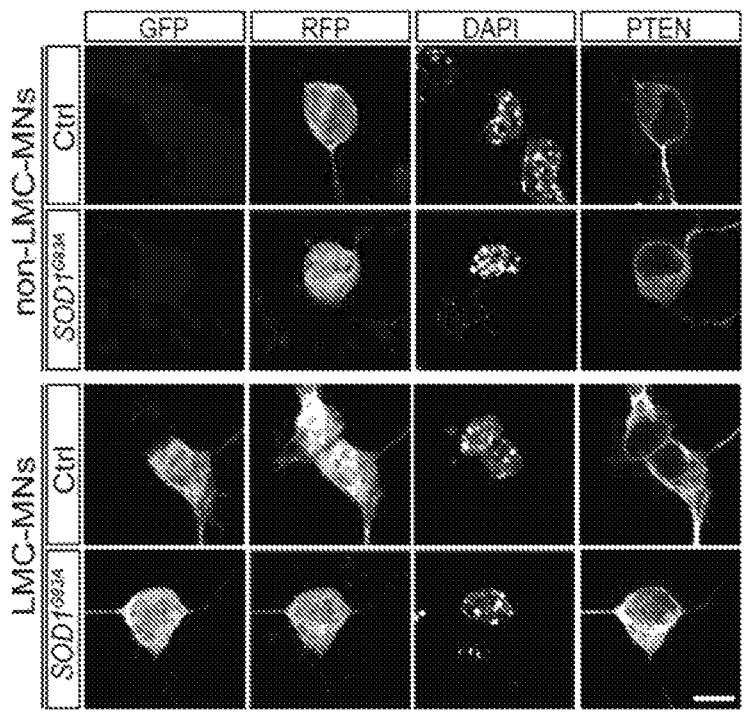
FIGS. 4A to 4E show that SOD1$^{G93A}$ LMC-MNs manifest early nuclear translocation of PTEN, resulting in their vulnerability to ALS.
Figure 4B:
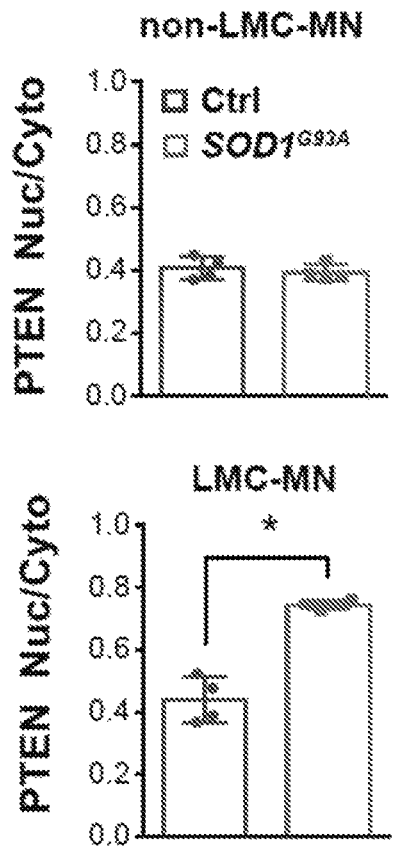

Next, we investigated changes in the subcellular localization of PTEN in LMC-MNs and non-LMC-MNs derived from both Ctrl and SOD1$^{G93A}$ mice at 24 hours post-CPA treatment. PTEN was mainly distributed in the cytosol in the Ctrl sets of both non-LMC-MNs and LMC-MNs (FIG. 4A), similar to our observations of adult spinal MNs (FIG. 2I). In accordance with our model, we observed a significant increase in the PTEN$^{nucleus/cytosol}$ ratio in SOD1$^{G93A}$ LMC-MNs upon stressor treatment compared to that of Ctrl LMC-MNs, whereas there was no difference in the PTEN$^{nucleus/cytosol}$ ratio of Ctrl and SOD1$^{G93A}$ non-LMC-MNs (FIG. 4A; quantification in FIG. 4B).

Figure 4C:
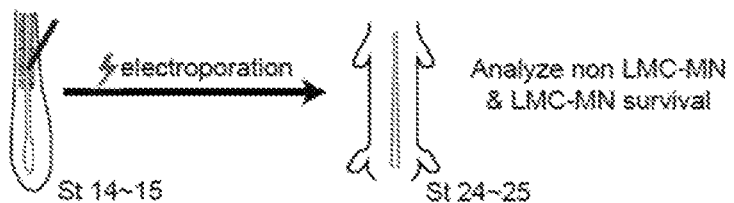
Figure 4D:
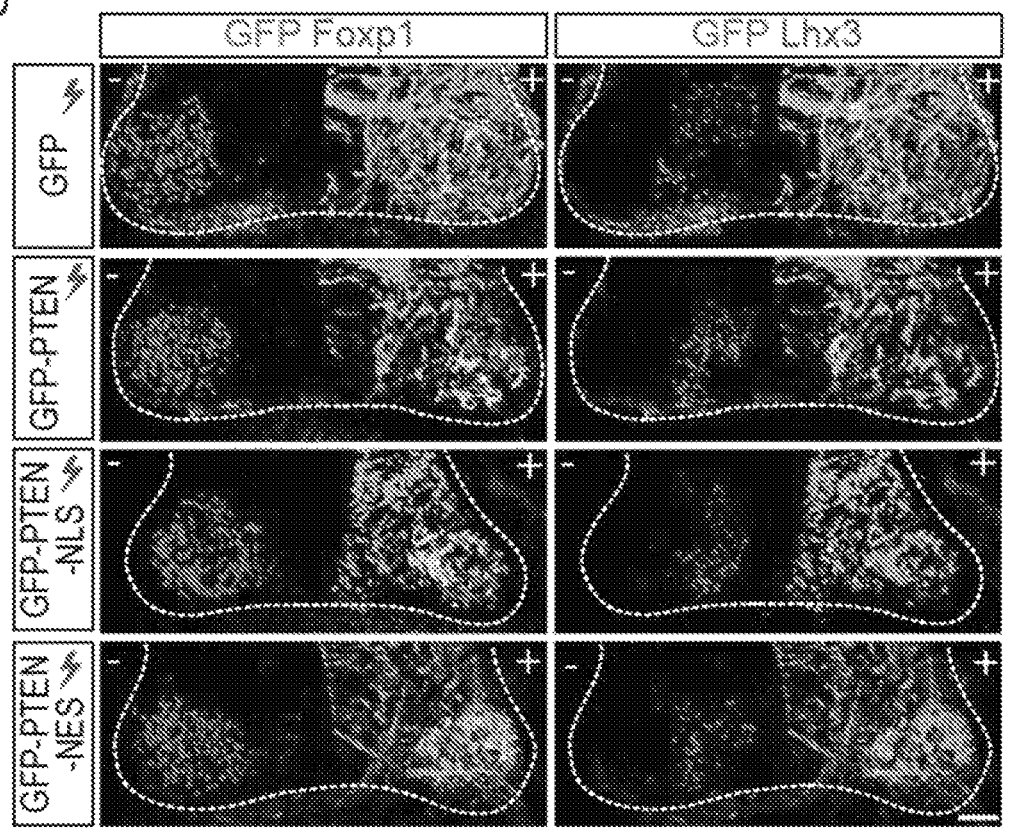
Figure 4E:
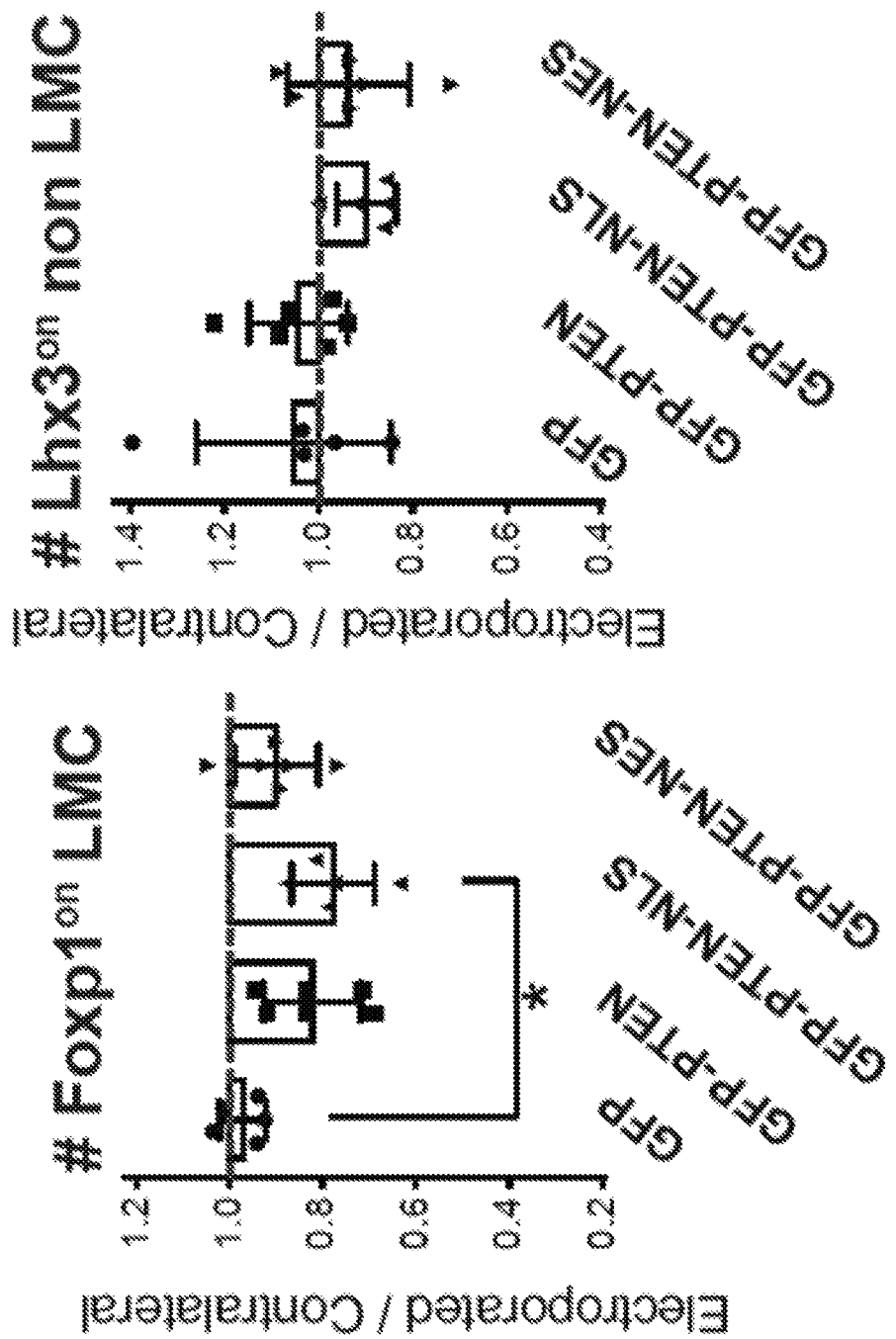

To further scrutinize if MN subtypes respond differentially to the cytotoxicity of nuclear PTEN, we adopted in ovo system by electroporation of PTEN fused with either nuclear localization or nuclear export signals (NLS and NES) into developing chicken embryos (FIG. 4C). Compared to marginal effects of PTEN-WT and PTEN-NES, ectopic overexpression of PTEN-NLS instead led to a significant loss of Foxp1$^{on}$ LMC-MNs. Interestingly, Lhx3$^{on}$ non LMC-MNs are more resistant to PTEN expression. This result indicates that nPTEN preferentially causes LMC-MN death (FIG. 4D, quantification in FIG. 4E).

Taken all together, these findings suggest that selective mir-17~92/nPTEN dysregulation occurs early in SOD1$^{G93A}$ LMC-MNs and confers the MN subtype vulnerability of ALS.

Example 5 Recapitulation of hsa-mir-17~92/nPTEN Dysregulation in Human ALS SOD1$^{+/L144F}$ iPSC-Derived MNs To further explore whether the role of mir-17~92 is relevant in a human MN context, we differentiated a human ESC line harboring the MN reporter Hb9::GFP (HuES3 HB9::GFP) into MNs under defined conditions (Maury, Y., Come, J., Piskorowski, R. A., Salah-Mohellibi, N., Chevaleyre, V., Peschanski, M., Martinat, C., and Nedelec, S. (2014). Combinatorial analysis of developmental cues efficiently converts human pluripotent stem cells into multiple neuronal subtypes. Nature biotechnology) that recapitulate the developmental temporal order from OLIG2$^{on}$ progenitor MNs (day 9) into HB9$^{on}$/ISL1$^{on}$ nascent MNs at day 14. Hb9::GFP$^{on}$ MNs were FACS-collected at day 16 and the enrichment of the LMC-MN markers were authenticated by FOXP1 and RALDH2 expressions. Similar to our finding in mouse MNs (FIG. 1F), hsa-mir-17~92 was expressed more abundantly in FACS-purified HB9::GFP$^{on}$ human MNs.

Next, we acquired human induced pluripotent stem cells (iPSCs) from ALS patients carrying the SOD1$^{+/L144F}$ mutation (Boulting, G. L., Kiskinis, E., Croft, G. F., Amoroso, M. W., Oakley, D. H., Wainger, B. J., Williams, D. J., Kahler, D. J., Yamaki, M., Davidow, L., et al. (2011). A functionally characterized test set of human induced pluripotent stem cells. Nature biotechnology 29, 279-286), and further generated an isogenic control SOD1$^{+/+}$ line mediated by CRISPR-Cas9 system to correct the mutated DNA sequence (FIGS. 5A and 5B). Both of these iPSC lines exhibited indistinguishable pluripotent hallmarks with normal karyotypes under our culture conditions, and SOD1 expression levels were comparable between the two lines. Both iPSC lines could be successfully differentiated into SMI32$^{on}$ ISL1$^{on}$ MNs with ~80% efficiencies following the developmental temporal order. Dissociated MNs were then cultured in neurotrophic factor (NF)-supplemented medium for another two weeks until manifesting a more matured marker CHAT. The majority (~75%) of ISL1$^{on}$ MNs acquired FOXP1$^{on}$ LMC-MN identity at day 16 and thereafter, providing an ideal system to study human LMC-MNs in ALS content.

Figures 5D, 5E:
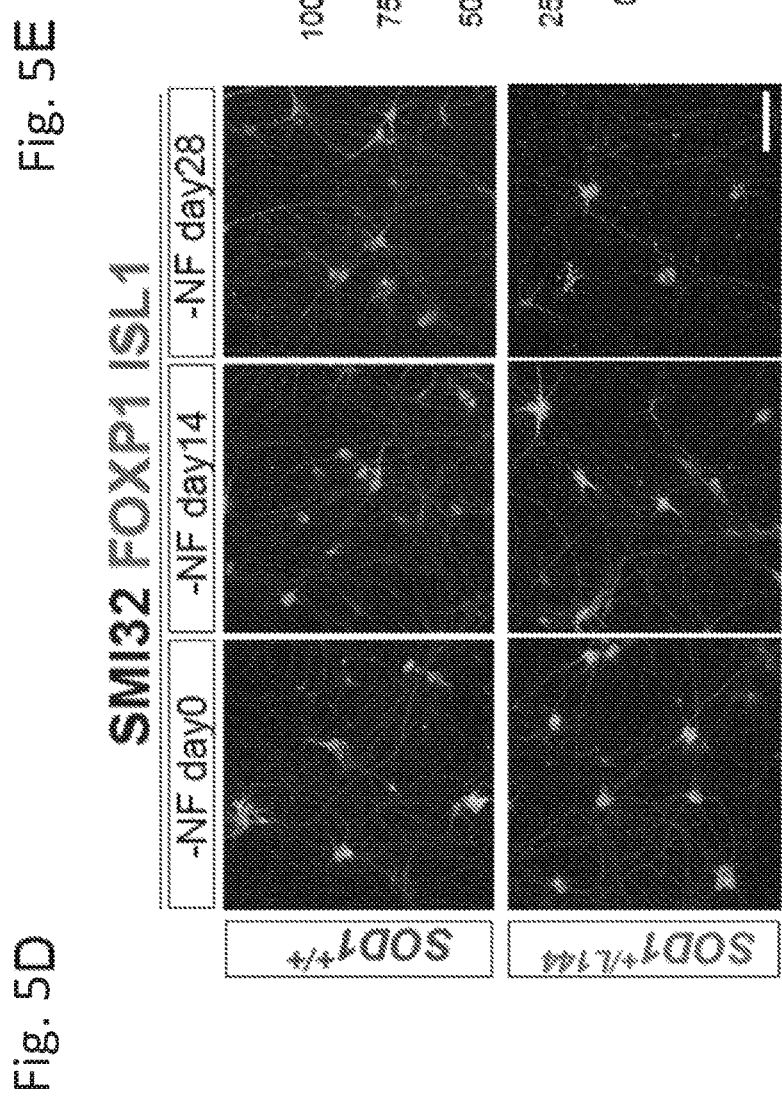
Figure 5F:
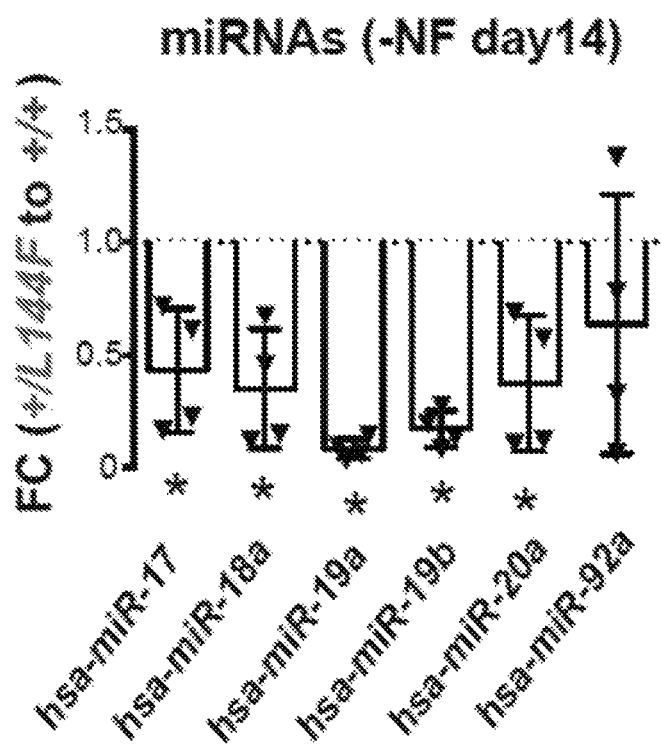

To accelerate ALS progression, we withdrew NFs in the media after MN maturation (from day 32~60) (Shi, Y., Lin, S., Staats, K. A., Li, Y., Chang, W. H., Hung, S. T., Hendricks, E., Linares, G. R., Wang, Y., Son, E. Y., et al. (2018). Haploinsufficiency leads to neurodegeneration in C9ORF72 ALS/FTD human induced motor neurons. Nature medicine 24, 313-325), resulting in a more prominent reduction of FOXP1$^{on}$ ISL1$^{on}$ LMC-MNs derived from ALS-SOD1$^{+/L144F}$ iPSCs (FIGS. 5C-5E). Next, we checked hsa-mir-17~92/nPTEN levels before and after 14 days of NF withdrawal, a stage before a severe loss of ALS-MNs, reminiscent to the onset of MN reduction in vivo. Indistinguishable expression of hsa-mir-17~92, PTEN and NDFIP1 protein levels, as well as nuclear-to-cytosolic ratio of PTEN in Ctrl-SOD1$^{+/+}$ and ALS-SOD1$^{+/L144F}$ MN cultures were observed before NF withdrawal. However, upon 14 days after NF withdrawal, there was a drastic reduction of the expression of hsa-mir-17~92 (FIG. 5F), concomitant with increased protein levels of PTEN, NEDD4-2 and NDFIP1, as well as enhancement of PTEN$^{nucleus/cytosol}$ ratio in ALS-SOD1$^{+/L144F}$ MN culture (FIGS. 5G and 5H). Notably, we did not observe significant difference in cell loss between the Ctrl-SOD1$^{+/+}$ and ALS-SOD1$^{+/L144F}$ lines at this stage (FIG. 5E). This finding corroborated the observations in mouse SOD1$^{G93A}$ model: the down-regulation of hsa-mir-17~92 with nuclear PTEN accumulation is exhibited prior to LMC-MN loss in SOD1-ALS type.

Figure 6A:
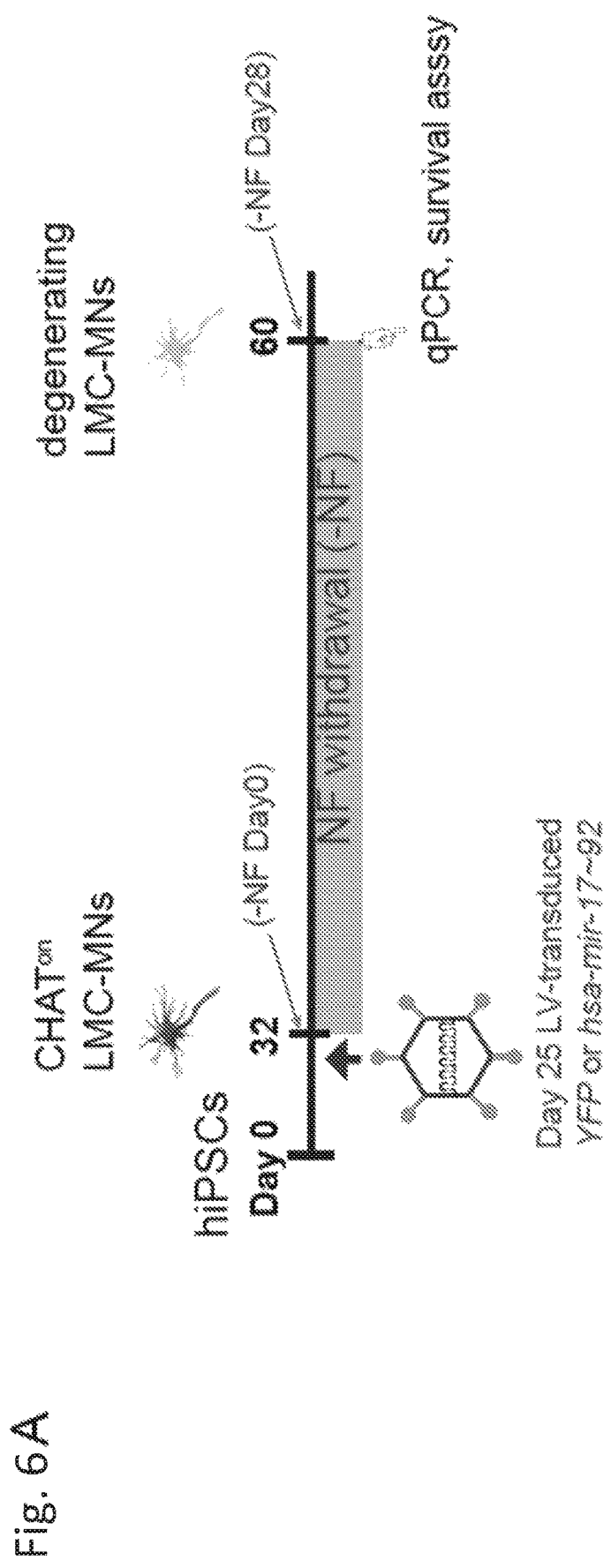
FIGS. 6A to 6E show that survival of SOD1$^{+/L144F}$ LMC-MNs can be extended by overexpression of hsa-mir-17~92.
Figure 6B:
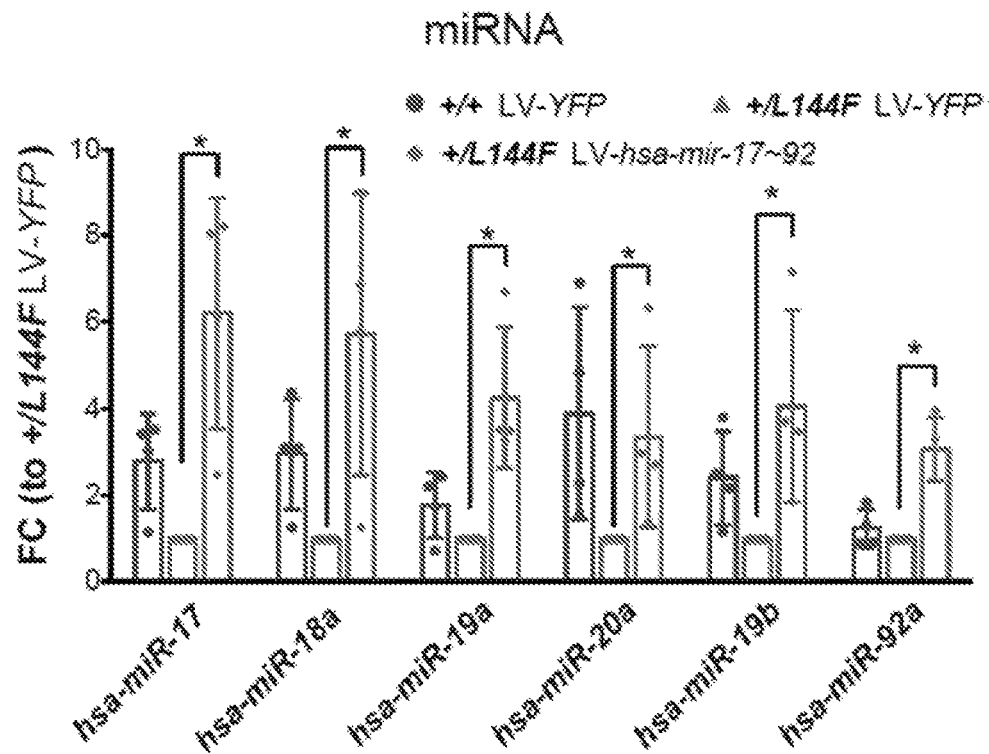
Figure 6C:
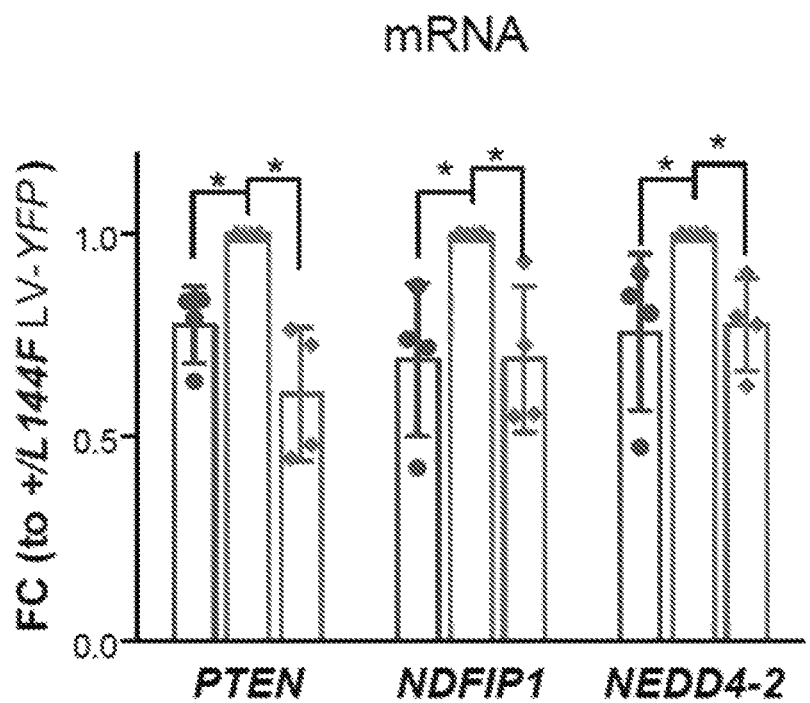
Figure 6D:
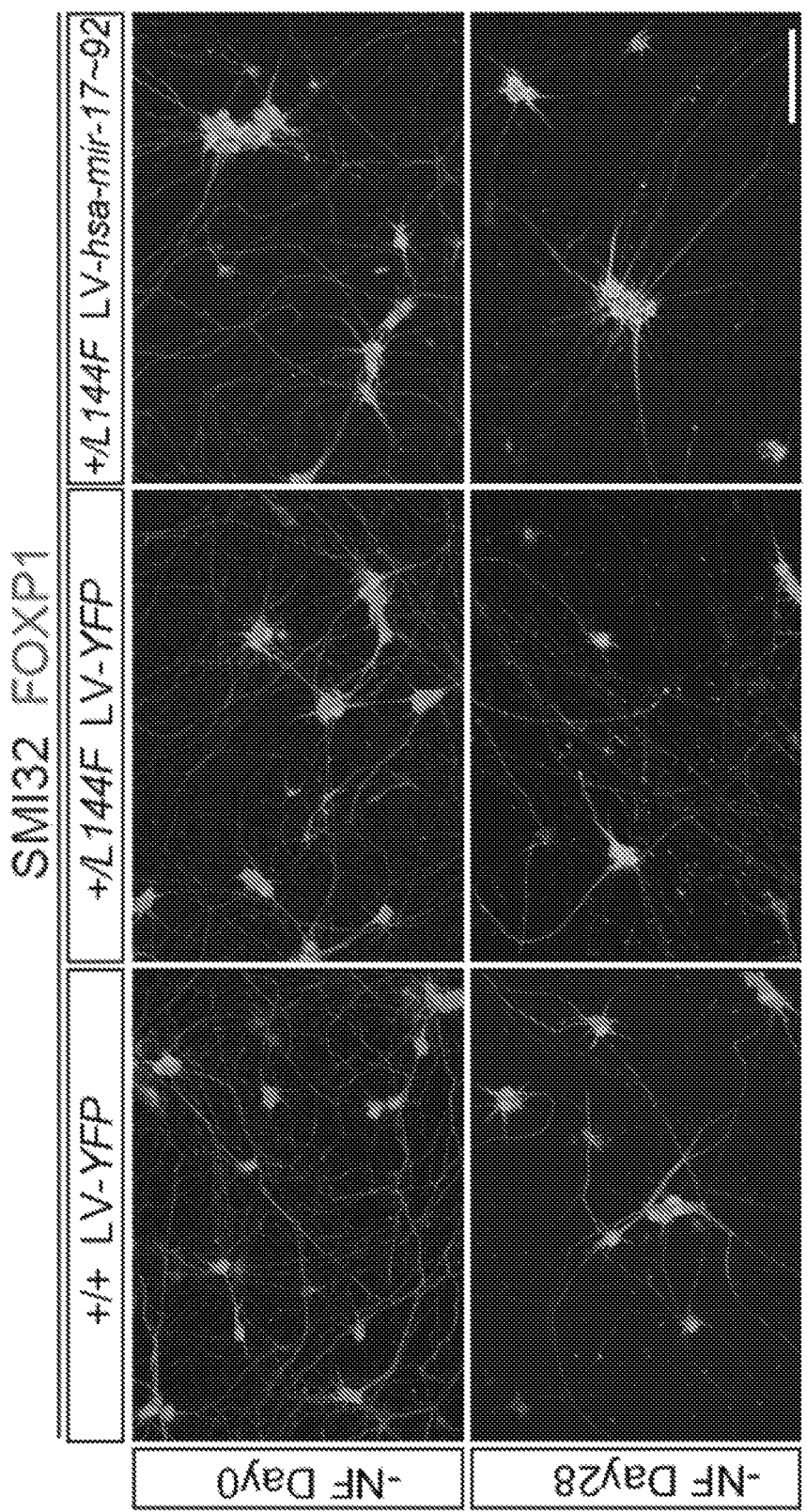
Figure 6:
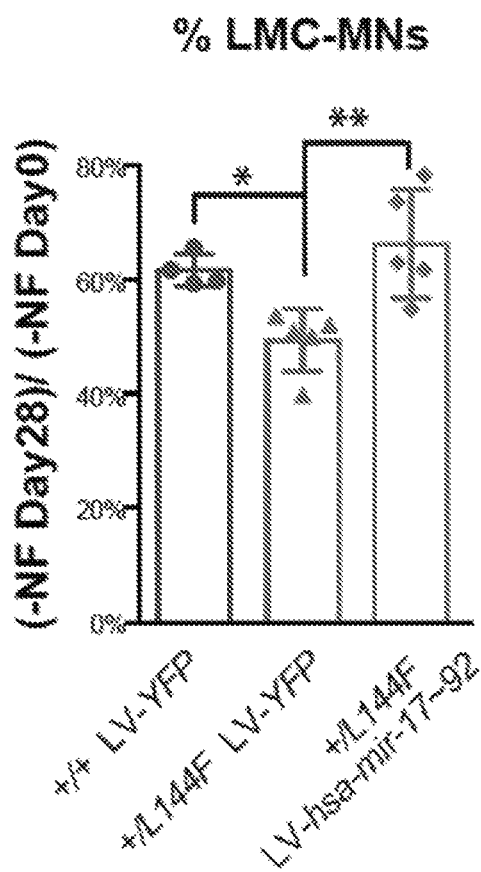

Example 6 Targeting hsa-mir-17~92 for Therapeutic Application in Human SOD1$^{+/L144F}$ iPSC-Derived MNs To exploit if mir-17~92 could serve as a target to spare MN degeneration in ALS, we then tested if manipulation of mir-17~92 expression could rescue MN degeneration in human ALS-iPSC derived MNs. We utilized lentivirus (LV) to deliver hsa-mir-17~92 or YFP as a control into iPSCMNs before NF withdrawal (FIG. 6A). The persistent overexpression of YFP and hsa-mir-17~92 in ALS-SOD1$^{+/L144F}$ MNs throughout the survival assay were confirmed by immunostaining and qPCR, respectively (FIG. 6B). As expected, ectopic hsa-mir-17~92 expression led to the repression of PTEN, NEDD4-2 and NDFIP1 in ALS-SOD1$^{+/L144F}$ MNs (FIG. 6C), with notable rescued effects on of ALS-SOD1$^{+/L144F}$ LMC-MN populations (FIG. 6D and quantification in 6E). Above all, these data supported that overexpression of hsa-mir-17~92 in MN context can relieve MN degeneration in ALS-SOD1$^{+/L144F}$, thereby providing proof-of-principle evidence that hsa-mir-17~92 could be an ideal therapeutic target for ALS treatment.

Figure 7:
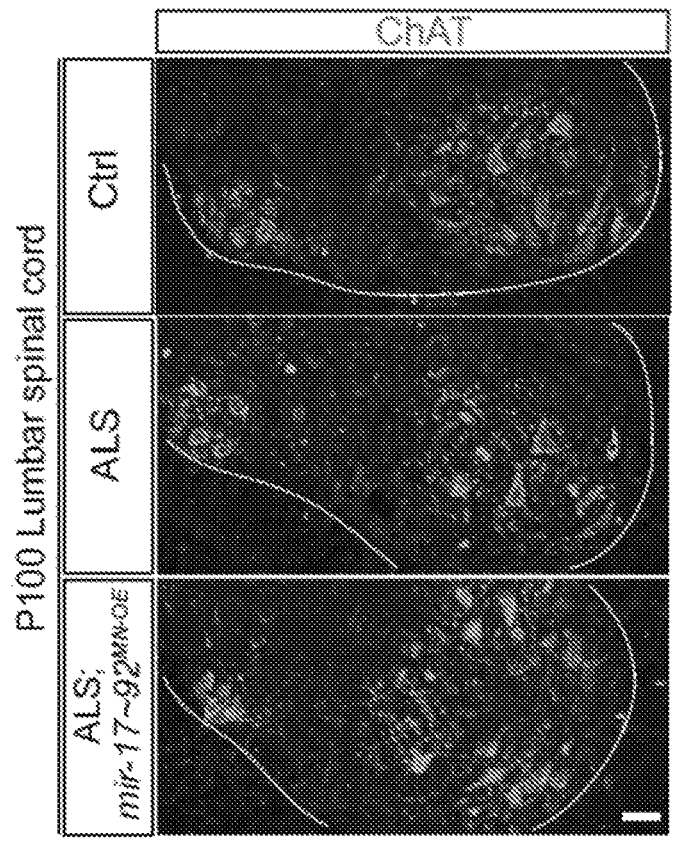
FIGS. 7A to 7H show that overexpression of mir-17~92 in MNs delays the onset of disease and extends lifespans of SOD1$^{G93A}$ mice.
Figure 7:
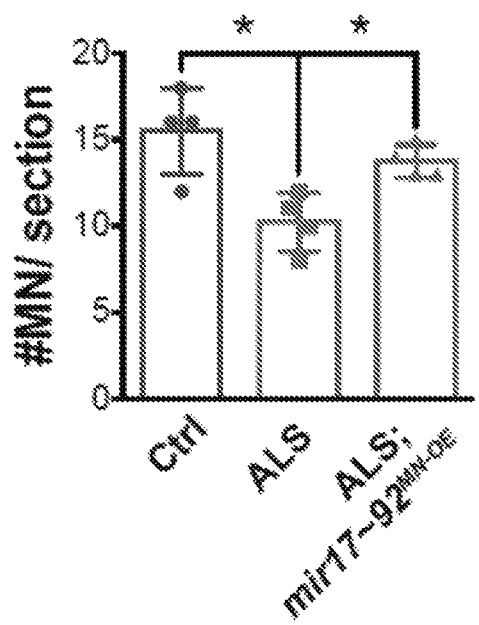
Figure 7D:
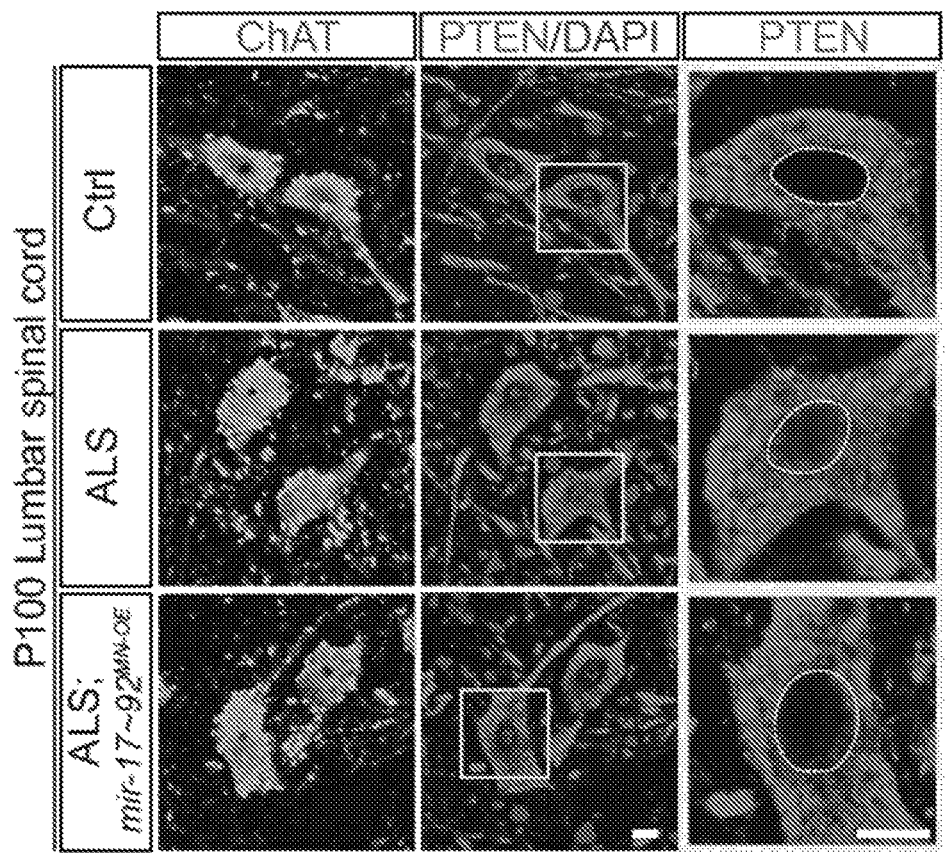
Figure 7E:
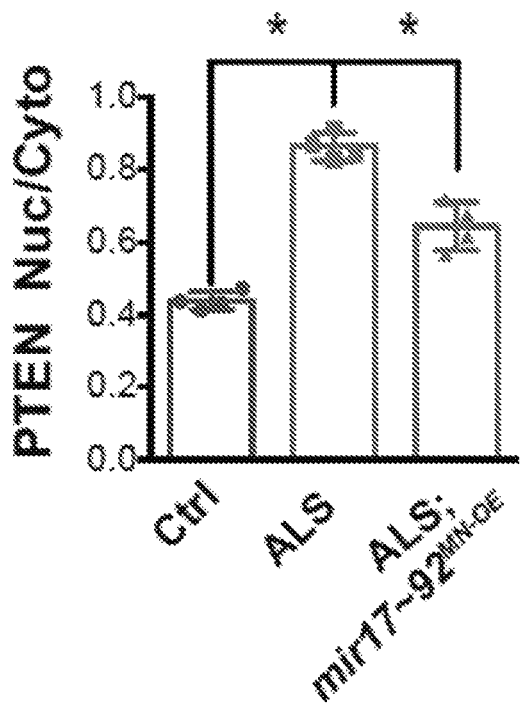

Example 7 Amelioration of ALS Symptoms in SOD1$^{G93A}$ Mice by Overexpressing mir-17~92 in MNs To exploit if mir-17~92 could rescue MN degeneration in ALS in vivo, we then tested if manipulation of mir-17~92 expression could ameliorate ALS symptoms in SOD1$^{G93A}$ mice. We have previously generated conditional mir-17~92$^{MN-OE}$ (Olig2$^{Cre/+}$; ROSA-26-LSL-mir-17~92$^{f/f}$) mice, and these mice were healthy and exhibited a normal lifespan (Tung, Y. T., Lu, Y. L., Peng, K. C., Yen, Y. P., Chang, M., Li, J., Jung, H., Thams, S., Huang, Y. P., Hung, J. H., et al. (2015). Mir-17~92 Governs Motor Neuron Subtype Survival by Mediating Nuclear PTEN. Cell reports 11, 1305-1318). Here, we further crossed mir-17~92$^{MN-OE}$ mice to the SOD1$^{G93A}$ strain in a pure C57BL/6 background (FIG. 7A). Restoration of mir-17~9 expression in ChAT$^{on}$ MNs was validated by in situ hybridization together with immunostaining of lumbar spinal cord sections of [SOD1$^{G93A}$; mir-17~92$^{MN-OE}$] mice. Compared to the barely detectable level of miR-17 expression in SOD1$^{G93A}$ siblings at P100, [SOD1$^{G93A}$; mir-17·92$^{MN-OE}$] mice retained high levels of miR-17 expression. As a consequence, the reduced MN numbers in SOD1$^{G93A}$ mice was significantly spared in [SOD1$^{G93A}$; mir 17~92$^{MN-OE}$] mice at P100 (FIG. 7B, quantification in 7C). At a molecular level, the elevated PTEN$^{nucleus/cytosol}$ ratio in SOD1$^{G93A}$ MNs was reduced upon mir-17~92 overexpression (FIG. 7D, quantification in 7E).

Figure 7F:
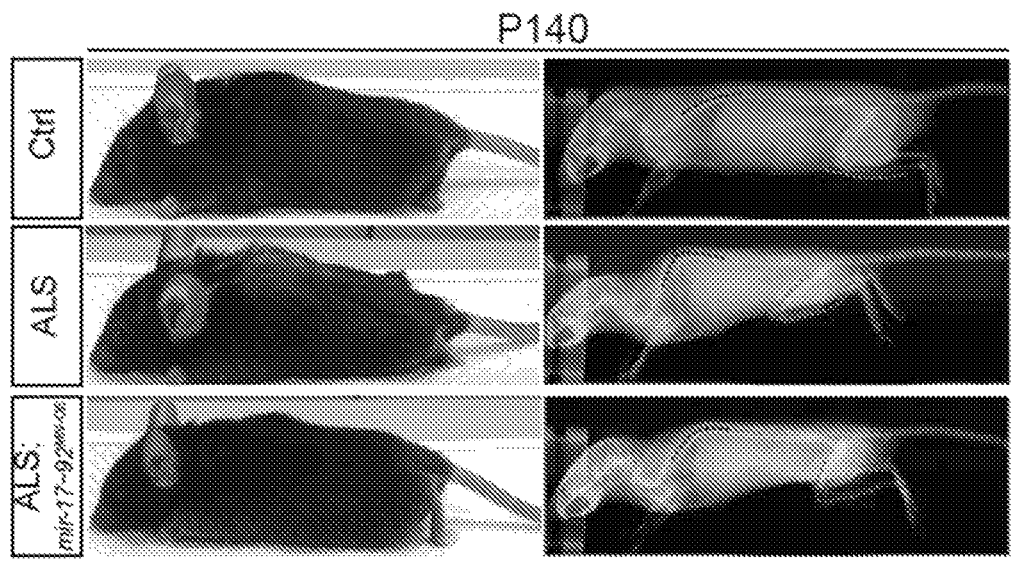
Figure 7G:
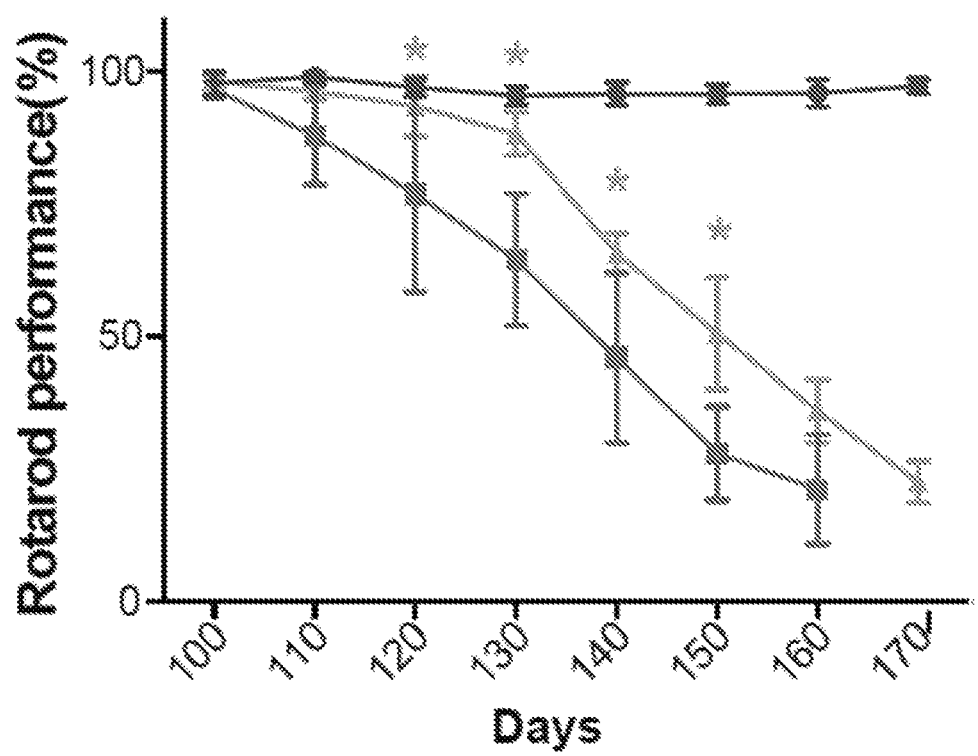
Figure 7H:
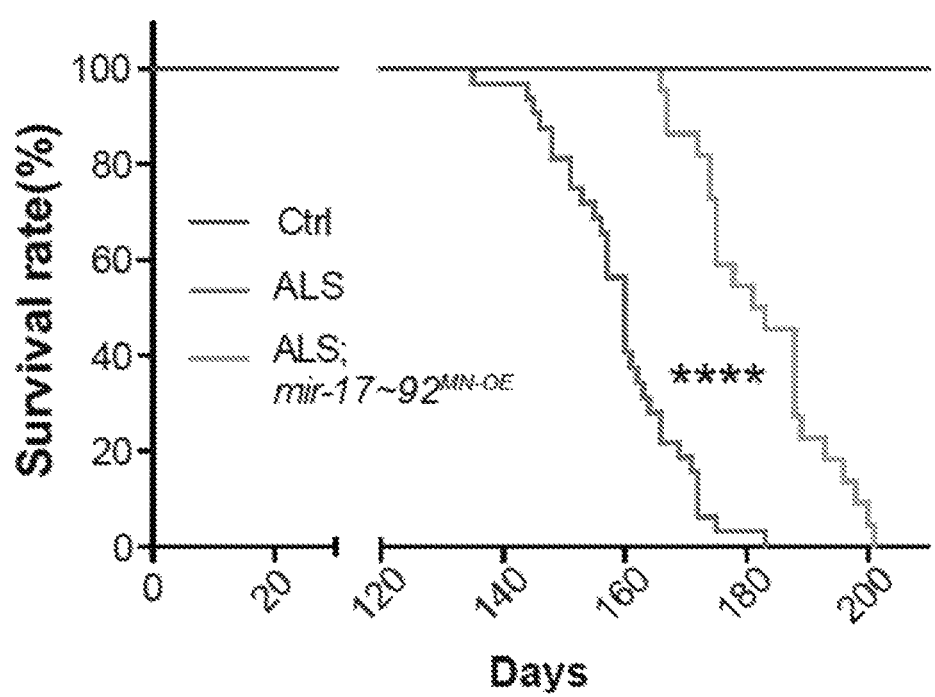

To further examine whether mir-17~92 overexpression improves ALS symptoms and motor function, we performed a series of physiological assays (Kanning, K. C., Kaplan, A., and Henderson, C. E. (2010). Motor neuron diversity in development and disease. Annual review of neuroscience 33, 409-440). [SOD1$^{G93A}$; mir-17~92$^{MN-OE}$] mice gained body weight and exhibited alleviated hindlimb clasping symptoms at P140. The kyphosis phenotype caused by muscle weakness in SOD1$^{G93A}$ mice was also ameliorated by mir-17~92 overexpression (examined by roentgenogram) (FIG. 7F). Behaviorally, [SOD1$^{G93A}$; mir-17~92$^{MN-OE}$] mice performed better in a rotarod test (FIG. 7G). Strikingly, median survival of SOD1$^{G93A}$ mice in our C57BL/6 colony was ~160 days, but this increased to 182 days on overexpression of mir-17~92, representing a ~14% increase in lifespan (FIG. 7H).

Figure 8A:
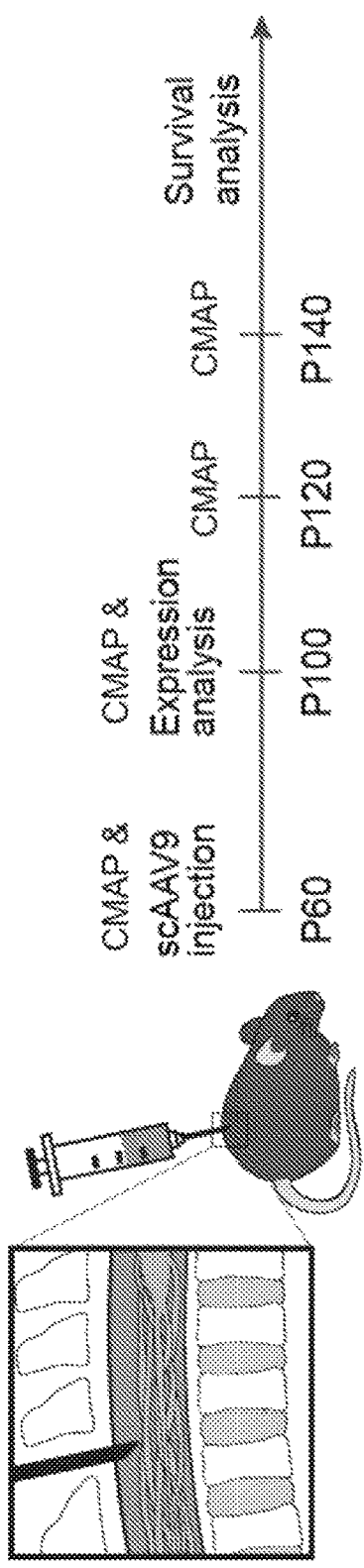
FIGS. 8A to 8E show that gene therapy of SOD1$^{G93A}$ mice by overexpressing mir-17~92 at adulthood is sufficient to protect neuromuscular function and extend lifespan.
Figure 8B:
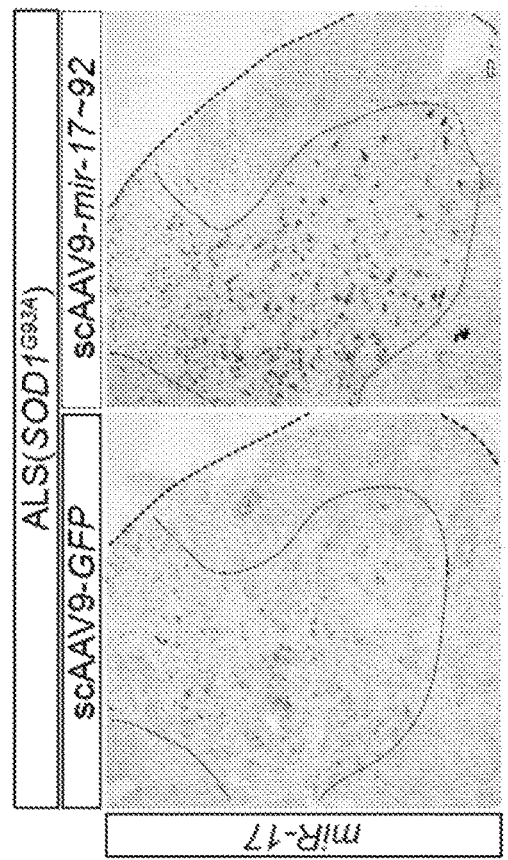
Figure 8C:
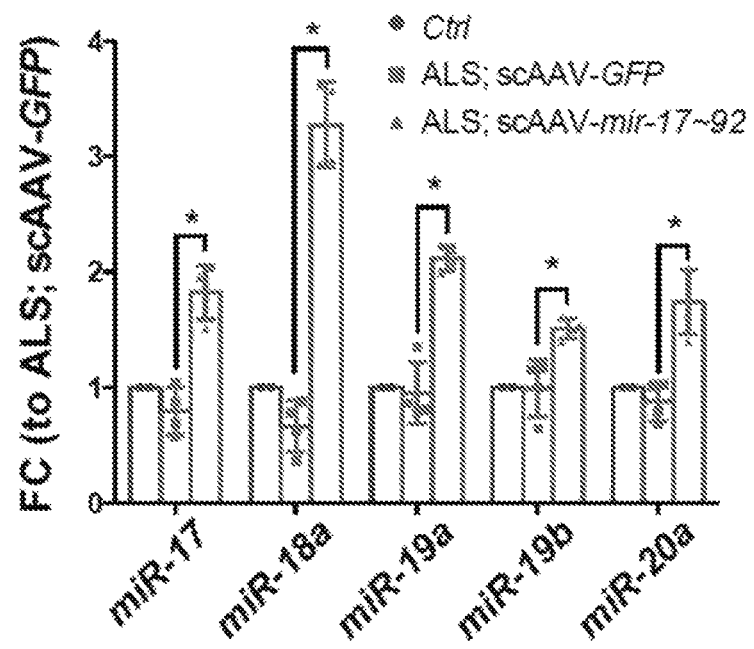

Example 8 Adult Administration of AAV9-mir17~92 Prolongs SOD1$^{G93A}$ Mice Survival The promising outcome of overexpressing mir-17~92 in SOD1$^{G93A}$ mice prompted us to test the potential of mir-17~92 as a therapeutic measure in adult mice. We utilized self-complementary adeno-associated vector serotype 9 (scAAV9) to overexpress mir-17~92 in the whole spinal cord by intrathecal injection at P60 (Foust, K. D., Salazar, D. L., Likhite, S., Ferraiuolo, L., Ditsworth, D., Ilieva, H., Meyer, K., Schmelzer, L., Braun, L., Cleveland, D. W., et al. (2013). Therapeutic AAV9-mediated suppression of mutant SOD1 slows disease progression and extends survival in models of inherited ALS. Molecular therapy: the journal of the American Society of Gene Therapy 21, 2148-2159), which bypassed the potential function of mir-17~92 to promote ectopic proliferation of embryonic MN progenitors (FIG. 8A). To test the efficiency of virus infection, we first injected scAAV9-GFP to Ctrl mice and observed strong and sustained GFP expression in spinal MNs as well as in some dorsal cells at 40 days post-injection. Then, scAAV9-mir-17~92 was injected in parallel to scAAV9-GFP into Ctrl and SOD1$^{G93A}$ mice. We verified robust induction of exogenous mir-17~92 in the spinal cord by in situ hybridization of miR-17, as well as qPCR quantification of mir-17~92 members in the lumbar spinal cord (FIGS. 8B and 8C).

Figure 8D:
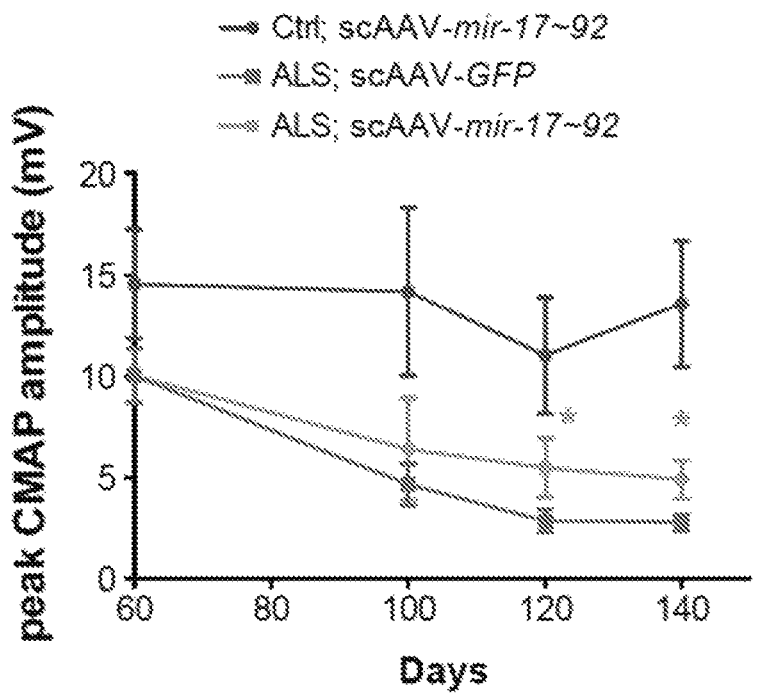
Figure 8E:
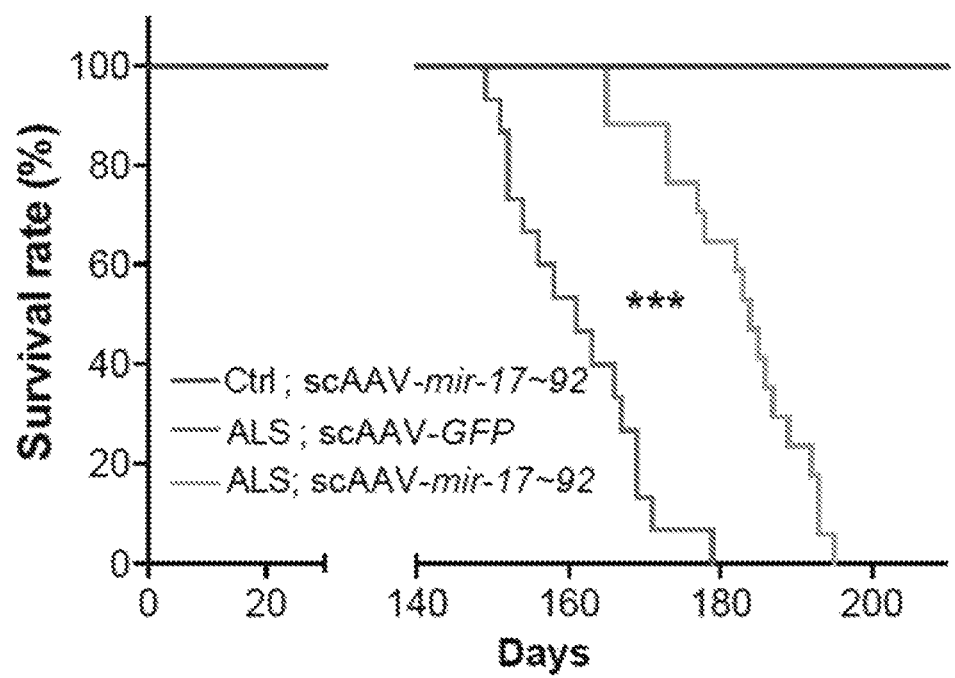

To evaluate the mice in a more clinically relevant setting, we assayed MN and gastrocnemius (GA) muscle connectivity by measuring CMAP. We performed CMAP at several time points: from P60 (right before the AAV treatment) to P140. SOD1$^{G93A}$ mice had just begun to manifest MN denervation at P60 and exhibited a slightly compromised CMAP amplitude. At P120 and P140, the CMAP response had significantly ameliorated upon AAV9-mir-17~92 treatment, but had not yet improved to the level of Ctrl mice (FIG. 8D). Unlike how SOD1 antisense oligonucleotide (ASO) treatment promotes MN reinnervation (McCampbell, A., Cole, T., Wegener, A. J., Tomassy, G. S., Setnicka, A., Farley, B. J., Schoch, K. M., Hoye, M. L., Shabsovich, M., Sun, L., et al. (2018). Antisense oligonucleotides extend survival and reverse decrement in muscle response in ALS models. J Clin Invest 128, 3558-3567), our data suggests that overexpression of mir-17~92 enhances MN survival significantly rather than promotes MN reinnervation. Finally, and most importantly, adult delivery of mir-17~92 also prolonged the lifespan of SOD1$^{G93A}$ mice from a median of 161 days to 184 days (FIG. 8E).

Taken all together, our results support that mir-17~92 is a sine qua non intrinsic regulator to sustain MN survival via regulating PTEN subcellular translocation in adult MNs. In the ALS content, overexpression of mir-17~92 in MNs by either a genetic approach or scAAV9 delivery in adults delays the onset of MN degeneration, enhances motor function, and increases the lifespan of our ALS mouse model. These findings envisage mir-17~92 to be a prognosis marker for MN degeneration and a promising candidate therapeutic target for ALS patients.

We claim:

1. A method of delaying an onset of motor neuron (MN) degeneration, reducing a risk of developing MN degeneration, or treating amyotrophic lateral sclerosis (ALS) associated with an SOD1 gene mutation in an adult subject bearing the SOD1 gene mutation, comprising administering to a central nervous system of the adult subject a therapeutically or prophylactically effective amount of genes or transgenes containing members of mir-17~92 cluster, wherein the members of the miR-17~92 cluster are miR-17, miR-17$^+$, miR-18a, miR-19a, miR-19b, miRr-20a, and miR-92a, and wherein the genes or transgenes are incorporated into or encapsulated in a viral vector.

2. The method of claim 1, wherein the administration delivers the genes or transgenes containing the members of mir-17~92 cluster into a spinal cord of the adult subject.

3. The method of claim 1, wherein the administration results in overexpression of the members of mir-17~92 cluster in SOD1G93A motor neurons (MNs).

4. The method of claim 1, wherein an early and selective down-regulation of mir-17~92 in SOD1G93A MNs precedes the onset of MN degeneration.

5. The method of claim 1, wherein the ALS is familial ALS or sporadic ALS.

6. The method of claim 1, wherein the transgenes further comprise an H1 promoter, CMV promoter, RSV promoter, SV40 promoter, human β-actin promoter, human elongation factor-1αpromoter or cytomegalovirus early enhancer/chicken β-actin promoter.

7. The method of claim 1, which further comprises administering one or more inhibitory nucleic acids targeting SOD1, a transgene encoding a nuclear PTEN interfering peptide, an ER stress inhibitor, a stress granule blocker or a miRNA biogenesis activator.

8. The method of claim 1, wherein the administration is intrathecal injection.

* * * * *